(12) United States Patent
Kim et al.

(10) Patent No.: US 12,122,732 B2
(45) Date of Patent: Oct. 22, 2024

(54) FUNCTIONALIZED POLYCYCLIC AROMATIC HYDROCARBON COMPOUND AND LIGHT-EMITTING DEVICE INCLUDING THE SAME

(71) Applicants: Samsung Electronics Co., Ltd., Suwon-si (KR); RESEARCH & BUSINESS FOUNDATION SUNGKYUNKWAN UNIVERSITY, Gyeonggi-do (KR)

(72) Inventors: Sangwon Kim, Seoul (KR); Changsik Song, Suwon-si (KR); Juhyen Lee, Suwon-si (KR); Hyejin Cho, Suwon-si (KR); Hyeonjin Shin, Suwon-si (KR); Minsu Seol, Seoul (KR); Dongwook Lee, Suwon-si (KR)

(73) Assignees: Samsung Electronics Co., Ltd., Gyeonggi-do (KR); Research & Business Foundation Sungkyunkwan University, Gyeonggi-do (KR)

( * ) Notice: Subject to any disclaimer, the term of this patent is extended or adjusted under 35 U.S.C. 154(b) by 605 days.

(21) Appl. No.: 17/211,174

(22) Filed: Mar. 24, 2021

(65) Prior Publication Data
US 2021/0300845 A1  Sep. 30, 2021

(30) Foreign Application Priority Data

Mar. 25, 2020 (KR) .......................... 10-2020-0036443

(51) Int. Cl.
  *C07C 15/38* (2006.01)
  *H01L 51/00* (2006.01)
(Continued)

(52) U.S. Cl.
  CPC ........... *C07C 15/38* (2013.01); *H10K 85/622* (2023.02); *H10K 85/624* (2023.02); *H10K 50/15* (2023.02);
(Continued)

(58) Field of Classification Search
None
See application file for complete search history.

(56) References Cited

U.S. PATENT DOCUMENTS 7,718,997 B2    5/2010  Lonkin et al.
9,461,227 B2   10/2016  Kim et al.
(Continued)

FOREIGN PATENT DOCUMENTS

JP      2006/176491 A    7/2006
KR      101980194 B1     5/2019
(Continued)

OTHER PUBLICATIONS

Machine English translation of Yamada et al. (WO 2018/186462 A1). Sep. 27, 2023.*

(Continued)

*Primary Examiner* — Jay Yang
(74) *Attorney, Agent, or Firm* — HARNESS, DICKEY & PIERCE, P.L.C.

(57) ABSTRACT

Provided are a functionalized polycyclic aromatic hydrocarbon compound and a light-emitting device including the same. The functionalized polycyclic aromatic hydrocarbon compound is structurally stable, and exhibits high light-emission characteristics since aggregation caused by π-π stacking is inhibited, and thus may have high efficiency and long lifespan characteristics.

15 Claims, 20 Drawing Sheets

PICKET-FENCE

(51) Int. Cl.
  *H10K 85/60* (2023.01)
  *H10K 50/15* (2023.01)
  *H10K 50/16* (2023.01)
  *H10K 50/17* (2023.01)
  *H10K 50/18* (2023.01)

(52) U.S. Cl.
  CPC .......... *H10K 50/16* (2023.02); *H10K 50/171* (2023.02); *H10K 50/18* (2023.02)

(56) References Cited

U.S. PATENT DOCUMENTS

| | | |
|---|---|---|
| 2008/0105865 A1 | 5/2008 | Oyamada et al. |
| 2011/0256386 A1 | 10/2011 | Shi et al. |
| 2015/0167148 A1 | 6/2015 | Sutter et al. |
| 2017/0268123 A1 | 9/2017 | Hwang |

FOREIGN PATENT DOCUMENTS

| | | | |
|---|---|---|---|
| WO | WO-2018/186101 A1 | | 10/2018 |
| WO | WO-2018/186462 A1 | * | 10/2018 |

OTHER PUBLICATIONS

Akimitsu Narita et al., 'Synthesis of structurally well-defined and liquidphase-processable graphene nanoribbons' *Nature Chemistry*, vol. 6, Feb. 2014, pp. 126-132.

Shilpa Setia and Santanu Kumar Pal, 'Unsymmetrically substituted room temperature discotic liquid crystals based on hexa-peri-hexabenzocoronene core' ChemistrySelect, vol. 5, 2016, pp. 880-885.

J. N. Moorthy et al., 'Abundant Lattice Inclusion Phenomenon with Sterically Hindered and Inherently Shape-Selective Tetraarylpyrenes' *Journal of Organic Chemistry*, vol. 74, 2009, pp. 8566-8577.

J. N. Moorthy et al., 'Steric Inhibition of π-Stacking: 1,3,6,8-Tetraarylpyrenes as Efficient Blue Emitters in Organic Light Emitting Diodes (OLEDs)' Organic Letters, vol. 9, No. 25, 2007, pp. 5215-5218.

* cited by examiner

FUNCTIONALIZED POLYCYCLIC AROMATIC HYDROCARBON COMPOUND AND LIGHT-EMITTING DEVICE INCLUDING THE SAME

CROSS-REFERENCE TO RELATED APPLICATION

This application claims the benefit of Korean Patent Application No. 10-2020-0036443, filed on Mar. 25, 2020, in the Korean Intellectual Property Office, the disclosure of which is incorporated herein in its entirety by reference.

BACKGROUND

1. Field

The present disclosure relates to a functionalized polycyclic aromatic hydrocarbon compound and a light-emitting device including the same.

2. Description of Related Art

Organic light-emitting devices are self-emission devices that produce full-color images, and also have wide viewing angles, high contrast ratios, short response times, and excellent characteristics in terms of brightness, driving voltage, and response speed, compared to devices in the art.

In an example, an organic light-emitting device includes an anode, a cathode, and an organic layer that is disposed between the anode and the cathode and includes an emission layer. A hole transport region may be between the anode and the emission layer, and an electron transport region may be between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons transit from an excited state to a ground state, thereby generating light.

Research is continuing on light-emitting materials, in particular, organic light-emitting materials having high efficiency and a long lifespan.

SUMMARY

Provided are a functionalized polycyclic aromatic hydrocarbon compound and a light-emitting device including the same.

Additional aspects will be set forth in part in the description which follows and, in part, will be apparent from the description, or may be learned by practice of the presented embodiments.

According to an aspect of an embodiment, provided is a functionalized polycyclic aromatic hydrocarbon compound represented by any one of Formulae 1 to 7:

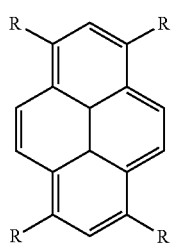

<Formula 1>

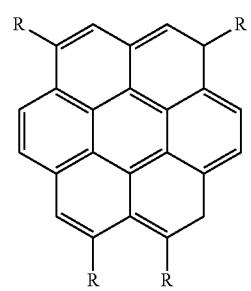

<Formula 2>

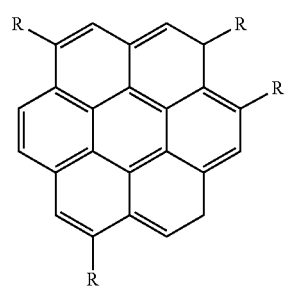

<Formula 3>

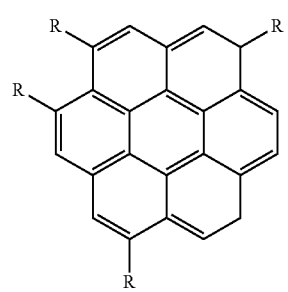

<Formula 4>

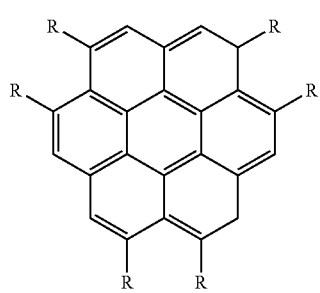

<Formula 5>

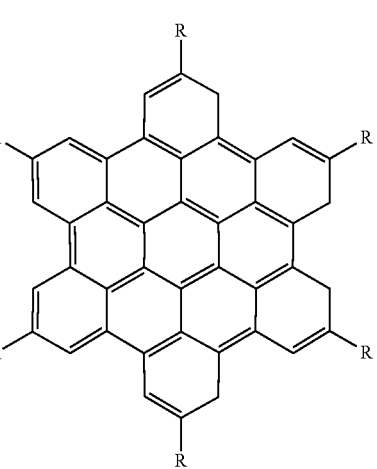

<Formula 6>

<Formula 7>

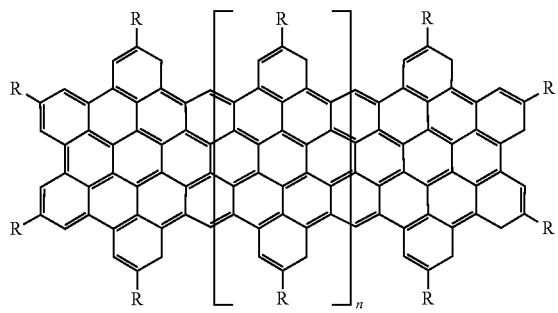

In Formulae 1 to 7,
R is

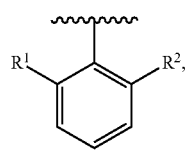

$R^1$ and $R^2$ are each independently selected from a fluoro group (—F), a chloro group (—Cl), a bromo group (—Br), an iodo group (—I), a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$), $Q_1$ to $Q_7$ are each independently selected from hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, and in Formula 7 is an integer of 0 to 10.

According to an aspect of other embodiment, provided is a light-emitting material including at least one of the above-described functionalized polycyclic aromatic hydrocarbon compounds.

According to an aspect of another embodiment, provided is a light-emitting device including at least one of the above-described functionalized polycyclic aromatic hydrocarbon compounds.

According to an aspect of another embodiment, provided is an organic light-emitting device including: a first electrode; a second electrode; and an organic layer including an emission layer between the first electrode and the second electrode, wherein the organic layer includes at least one of the above-described functionalized polycyclic aromatic hydrocarbon compounds.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
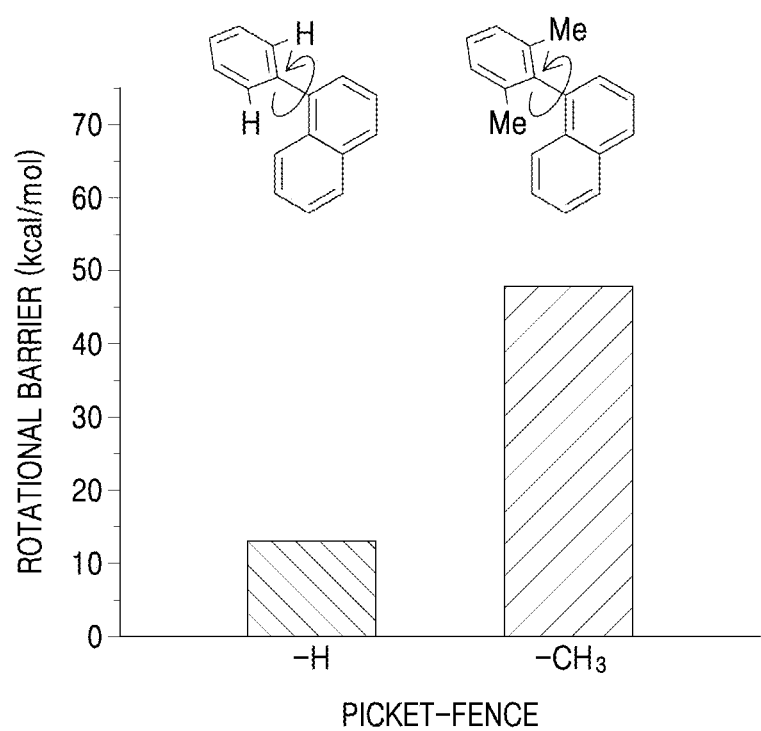
FIG. 1 is a graph showing rotational barriers of functional groups in an aromatic hydrocarbon compound.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

The present inventive concept will now be described more fully with reference to the accompanying drawings, in which example embodiments are shown. The present disclosure may, however, be embodied in many different forms, should not be construed as being limited to the embodiments set forth herein, and should be construed as including all modifications, equivalents, and alternatives within the scope of the present disclosure.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, parts, components, materials, and/or groups thereof.

In the drawings, the size or thickness of each layer, region, or element are arbitrarily exaggerated or reduced for better understanding or ease of description, and thus the present disclosure is not limited thereto. Throughout the written description and drawings, like reference numbers and labels will be used to denote like or similar elements. It will also be understood that when an element such as a layer, a film, a region, a component, or a plate is referred to as being "on" another layer or element, it can be "directly on" the other layer or element, or intervening layers, regions, or components may also be present. Although the terms "first", "second", etc., may be used herein to describe various elements, these elements should not be limited by these terms. These terms are used only to distinguish one component from another, not for purposes of limitation.

It will also be understood that although the terms "first", "second", etc., may be used herein to describe various elements, components, regions, layers, and/or domains, these elements, components, regions, layers, and/or domains should not be limited by these terms.

It will also be understood that the processes or steps described herein are not always applied in order. For example, in a case where a first step and a second step are described, it will be understood that the first step does not always precede the second step.

Hereinafter, example embodiments of a functionalized polycyclic aromatic hydrocarbon compound and a light-emitting device using the same will be described in greater detail.

A functionalized polycyclic aromatic hydrocarbon compound according to an embodiment is represented by any one of Formula 1 to 7.

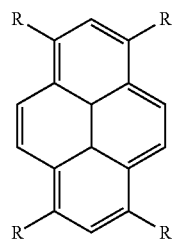

<Formula 1>

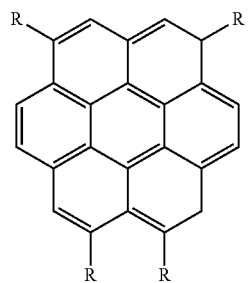

<Formula 2>

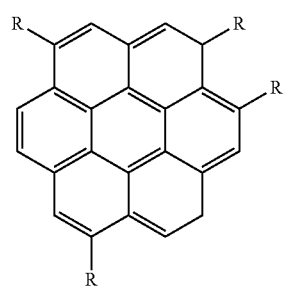

<Formula 3>

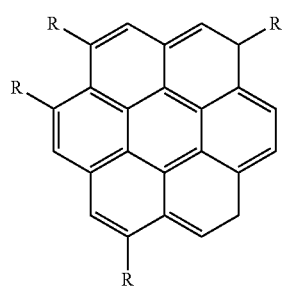

<Formula 4>

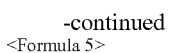

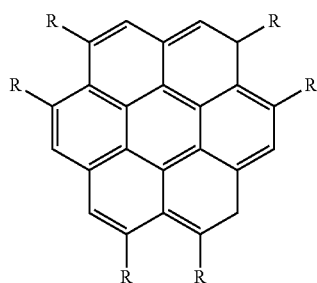

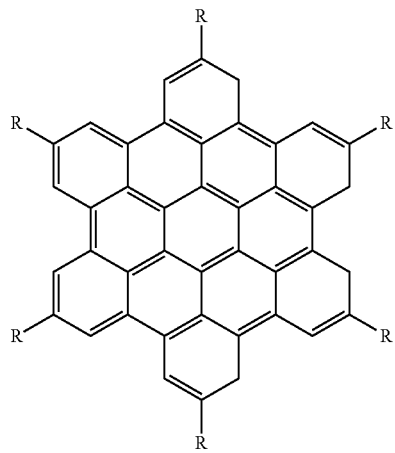

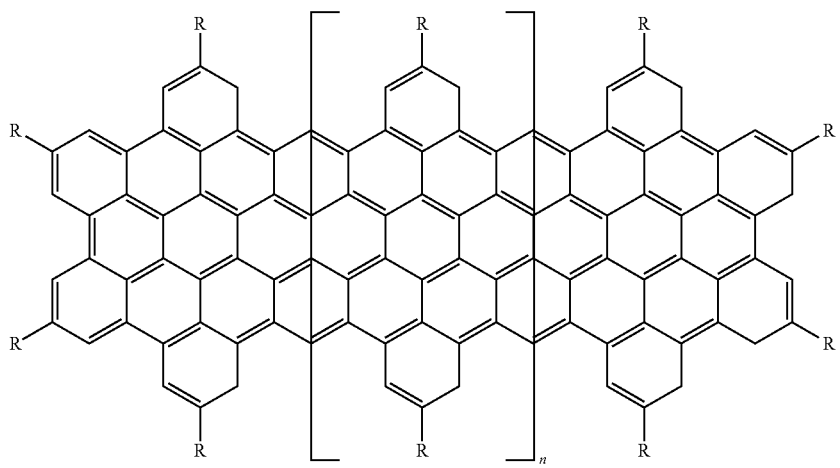

In Formulae 1 to 7,
R may be,

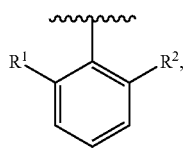

$R^1$ and $R^2$ may each independently be selected from a fluoro group (—F), a chloro group (—Cl), a bromo group (—Br), an iodo group (—I), a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$), $Q_1$ to $Q_7$ may each independently be selected from hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, and n may be an integer of 0 to 10.

The functionalized polycyclic aromatic hydrocarbon compounds represented by Formulae 1 to 7 may be structurally stable. In addition, since aggregation caused by π-π stacking is inhibited, the compounds may exhibit high emission characteristics. Accordingly, a light-emitting material having high efficiency and a long lifespan can be provided by the inclusion of a functionalized polycyclic aromatic hydrocarbon compound.

In existing polycyclic aromatic hydrocarbons (PAHs), even a small PAH such as pyrene may have a problem of luminescence quenching due to the aggregation caused by π-π stacking between molecules during film formation. In addition, a large PAH such as hexabenzocoronene or a larger PAH does not exhibit light-emission characteristics in a solution due to strong pi (π)-interactions.

Meanwhile, in the functionalized polycyclic aromatic hydrocarbon compound according to one or more embodiments, the edge of a core structure constituting the backbone is functionalized by phenyl groups having substituents $R^1$ and $R^2$ at 2- and 6-positions, such that π-π stacking in the core structure can be effectively limited and/or prevented to inhibit aggregation, and the functionalized polycyclic aromatic hydrocarbon compound may exhibit high luminous characteristics. The functionalized polycyclic aromatic hydrocarbon compound may exhibit excellent luminous characteristics even in a solution state, as well as in a solid state, due to the inhibition of π-π stacking.

Functional group R in Formulae 1 to 7 is a phenyl group having substituents $R^1$ and $R^2$ at 2- and 6-positions, and may have a greater π-π stacking inhibitory effect with a smaller volume as compared with aliphatic functional groups, and a reduced color shifting effect, in particular, red-shifting.

Functional group R in the functionalized polycyclic aromatic hydrocarbon compound may exhibit an excellent picket-fence effect due to a high rotational barrier and steric hindrance, and thus increase the interplanar distance of molecules to limit and/or prevent aggregation caused by π-π stacking. Here, the picket-fence effect means an effect in which, when an appropriate functional group is introduced into the edge of an aromatic hydrocarbon compound, the functional group increases the rotational barrier and steric hindrance to limit and/or prevent π-π stacking of the aromatic hydrocarbon compound.

The picket-fence effect will be described in greater detail with reference to FIGS. 1 and 2.

FIG. 1 is a graph showing rotational barriers of functional groups in an aromatic hydrocarbon compound. As shown in FIG. 1, an aromatic hydrocarbon compound such as naphthalene is found to have a higher rotational barrier when functionalized with 2,6-dimethylphenyl group as compared to when functionalized with a phenyl group.

Figure 2:
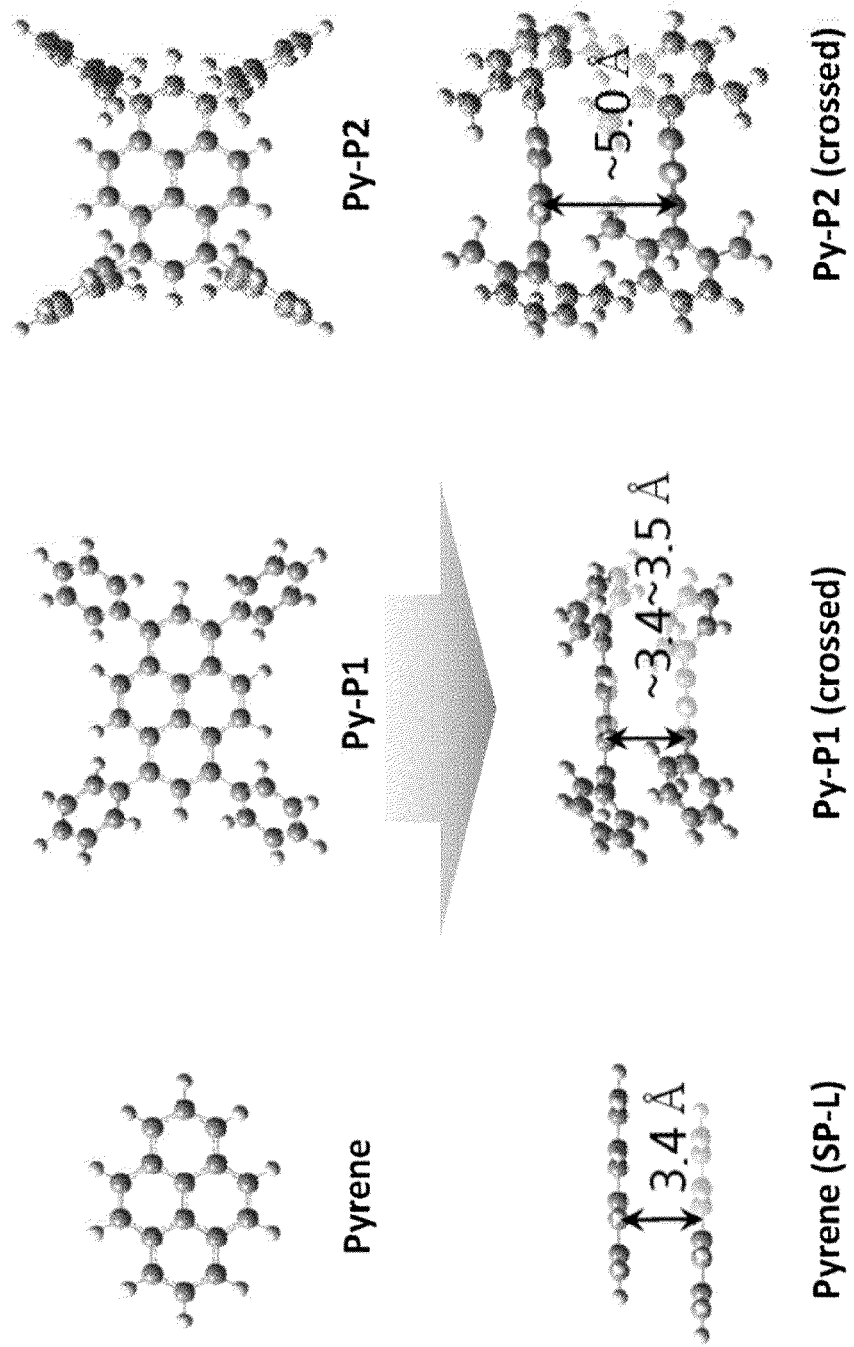
FIG. 2 illustrates simulated interplanar distances of functional groups, i.e., pyrene (denoted by Pyrene), phenylpyrene (denoted by Py-P1), and dimethylphenylpyrene (denoted by Py-P2)

FIG. 2 illustrates simulated interplanar distances of functional groups, i.e., pyrene (denoted by Pyrene), phenylpyrene (denoted by Py-P1), and dimethylphenylpyrene (denoted by Py-P2). As shown in FIG. 2, pyrene exhibits an interplanar distance of about 3.4 Å when stacked as planes, and phenylpyrene (Py-P1) of which the edge is functionalized with phenyl groups exhibits an interplanar distance of about 3.4 to 3.5 Å in the stacked structure due to the picket-fence effect of the phenyl groups. Dimethylphenylpyrene (Py-P2) of which the edge is functionalized with dimethylphenyl groups exhibits an increased interplanar distance of about 5 Å between the planes stacked crossed with the core structure of pyrene, due to the high rotational barrier and high steric hindrance of dimethylphenyl groups. The dimethylphenyl groups are found to exhibit a higher-picket-fence effect due to having a larger molecular size than the phenyl groups.

As described above, by inclusion of the functionalized polycyclic aromatic hydrocarbon compound with the edge functionalized with functional groups exhibiting a high rotational barrier and steric hindrance, due to inhibition of the aggregation caused by π-π stacking in the compound, a light-emitting material according to an embodiment may exhibit high luminous characteristics in solution or in a film, and have high efficiency and long lifespan characteristics.

The light-emitting material according to an embodiment may include, as the functionalized polycyclic aromatic hydrocarbon compound, at least one of a compound of Formula 1 having pyrene as the core structure, compounds of Formula 2 to 5 each having coronene as the core structure, a compound of Formula 6 having hexabenzocoronene as the core structure, and a compound of Formula 7 having graphene nanoribbons as the core structure.

In Formulae 1 to 7, functional group R may be

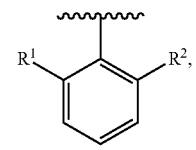

having substituents at 2- and 6-positions. Here, $R^1$ and $R^2$ may each independently be selected from a fluoro group (—F), a chloro group (—Cl), a bromo group (—Br), an iodo group (—I), a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{30}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$), wherein $Q_1$ to $Q_7$ may each independently be selected from hydrogen, a $C_1$-$C_{10}$ alkyl group, a $C_2$-$C_{10}$ alkenyl group, a $C_2$-$C_{10}$ alkynyl group, a $C_1$-$C_{10}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{30}$ arylthio group, a $C_2$-$C_{30}$ heteroaryl group, a monovalent non-aromatic condensed polycyclic group, and a monovalent non-aromatic condensed heteropolycyclic group.

In one or more embodiments, in functional group R, $R^1$ and $R^2$ may each independently be a fluoro group (—F), an unsubstituted $C_1$-$C_{10}$ alkyl group, an unsubstituted $C_6$-$C_{10}$ aryl group, a $C_1$-$C_{10}$ alkyl group substituted with a fluoro group, or a $C_6$-$C_{10}$ aryl group substituted with a fluoro group. For example, $R^1$ and $R^2$ may each independently be an unsubstituted $C_1$-$C_5$ alkyl group. For example, in functional group R, $R^1$ and $R^2$ may each independently be a methyl group, an ethyl group, an n-propyl group, an isopropyl group, an n-butyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, or a 3-methyl-2-butyl group. For example, in functional group R, $R^1$ and $R^2$ may each independently be a methyl group or an ethyl group, for example, a methyl group.

In one or more embodiments, the compounds represented by Formulae 1 to 6 may have one to six R functional groups including groups $R^1$ and $R^2$ each being an unsubstituted $C_1$-$C_5$ alkyl group, and the compound represented by Formula 7 may have six or more Rs having $R^1$ and $R^2$ each being an unsubstituted $C_1$-$C_5$ alkyl group. However, embodiments are not limited thereto. For example, the compound represented by Formula 1 may have one to four Rs, for example, two to four Rs, for example, four Rs, each R having $R^1$ and $R^2$ each being an unsubstituted $C_1$-$C_5$ alkyl group. For example, the compounds represented by Formula 2 to 6 may have two to six Rs, for example, three to six Rs, for example, four to six Rs, each R functional group including $R^1$ and $R^2$ each being an unsubstituted $C_1$-$C_5$ alkyl group. The compound represented by Formula 7 may have an edge that is uniformly functionalized according to the number of n, with the functional groups (R) each including $R^1$ and $R^2$ each being an unsubstituted $C_1$-$C_5$ alkyl group.

In one or more embodiments, the functionalized polycyclic aromatic hydrocarbon compound may include at least one compound from compounds represented by Formulae 1a to Formula 7c. However, embodiments are not limited thereto.

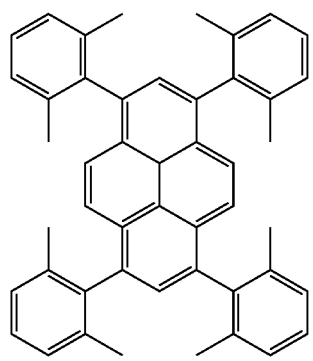
<Formula 1a>

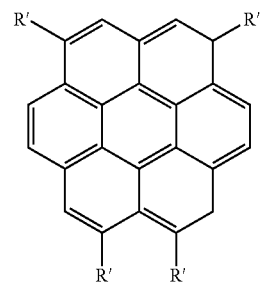
<Formula 2a>

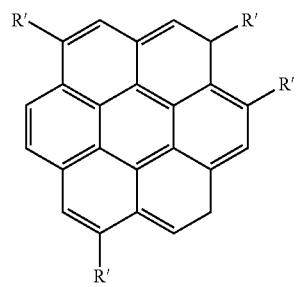
<Formula 3a>

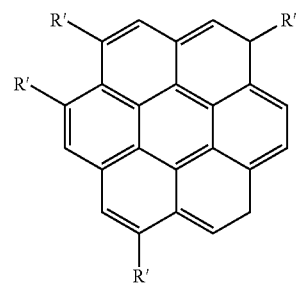
<Formula 4a>

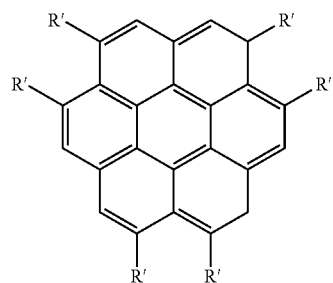
<Formula 5a>

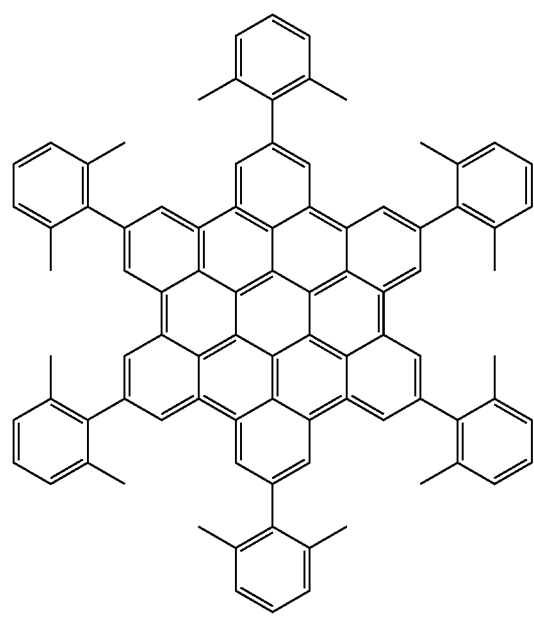
<Formula 6a>

<Formula 7a>
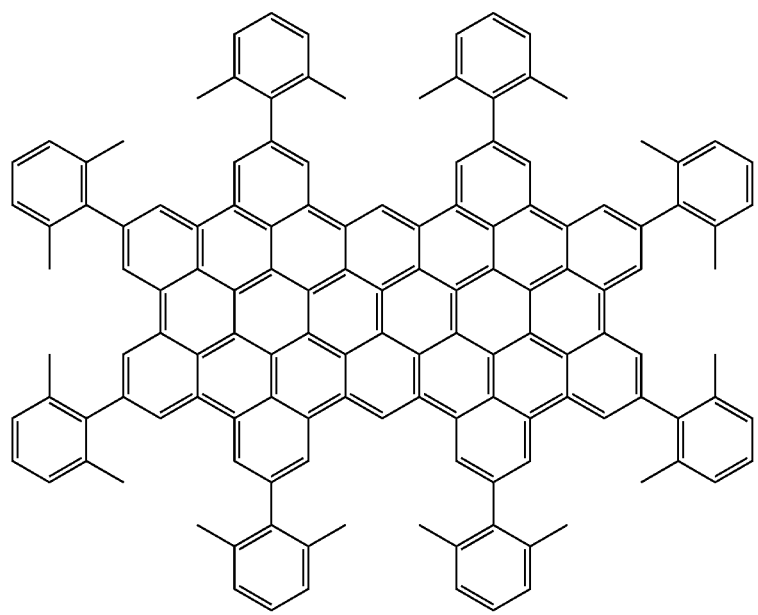
<Formula 7b>
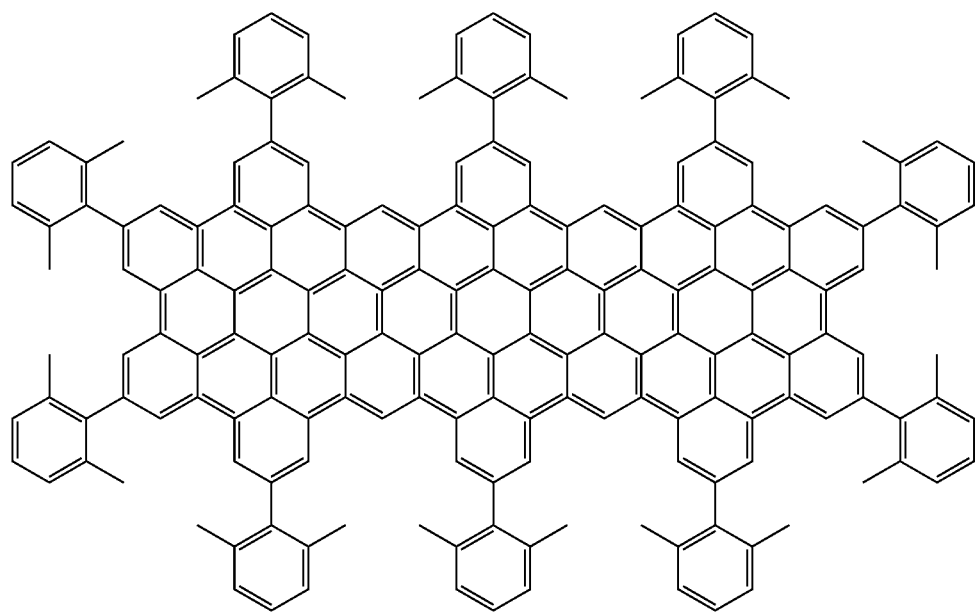

<Formula 7c>

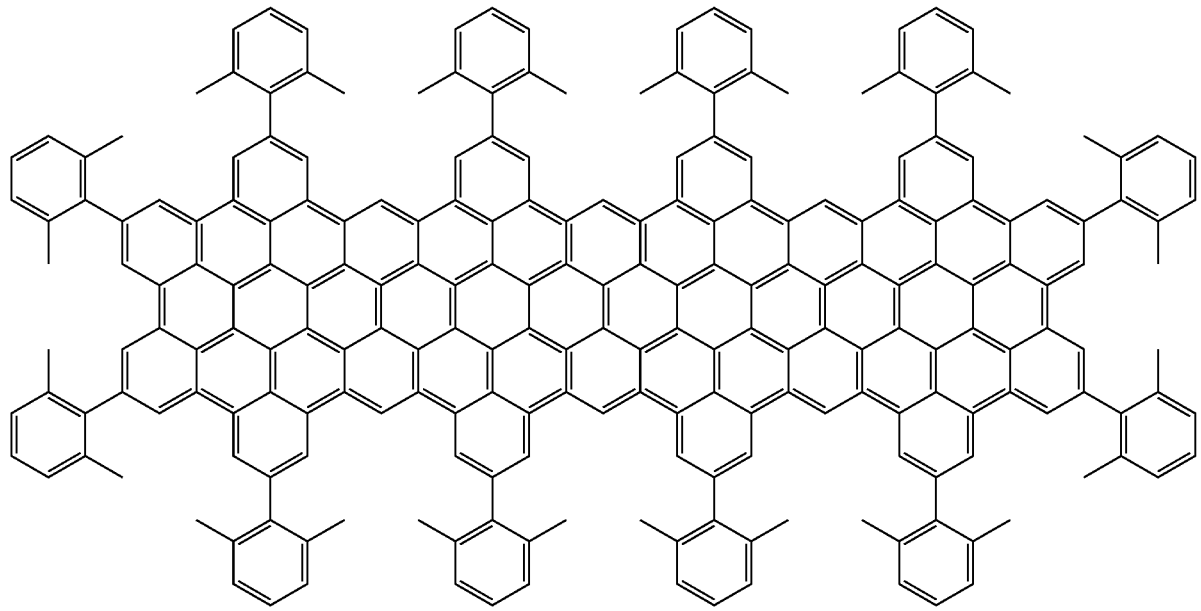

In Formulae 2a to 5b, R' may be

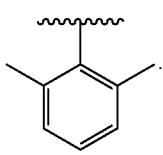

Synthesis methods of the functionalized polycyclic aromatic hydrocarbon compounds represented by Formula 1a to Formula 7c are easily recognizable by one of ordinary skill in the art with reference to the descriptions of the synthesis methods provided below.

The functionalized polycyclic aromatic hydrocarbon compounds represented by Formulae 1 to 7 may exhibit high emission characteristics in a solid state due to effective inhibition of π-π stacking, and exhibit a small color shift, particularly redshift, and may also exhibit high emission characteristics in solution due to improved solubility.

In one or more embodiments, the light-emitting material may include at least one functionalized polycyclic aromatic hydrocarbon compound represented by at least one of Formulae 1 to 7.

The light-emitting material may be provided in a solid state or solution state.

The light-emitting material may exhibit light emission of various wavelength bands by control of the core size of the functionalized polycyclic aromatic hydrocarbon compound. The larger the core size becomes, the emission wavelength may shift to the direction of red. The light-emitting material may exhibit light-emission characteristics in a wavelength range of about 350 nm to 650 nm according to the core size.

The light-emitting material including the functionalized polycyclic aromatic hydrocarbon compound may be used in various light-emitting devices such as organic light-emitting devices, light-emitting transistor devices, and the like.

In one embodiment, the functionalized polycyclic aromatic hydrocarbon compounds represented by Formulae 1 to 7 may be suitable for use as a host in organic layers of an organic light-emitting device, for example, as a host in an emission layer among organic layers. Accordingly, an organic light-emitting device including the functionalized polycyclic aromatic hydrocarbon compound may have high efficiency and/or a long lifespan.

In one or more embodiments, provided is an organic light-emitting device including: a first electrode; a second electrode; and an organic layer disposed between the first electrode and the second electrode and including an emission layer, wherein the organic layer includes at least one of the above-described functionalized polycyclic aromatic hydrocarbon compounds.

The organic light-emitting device may have high efficiency and a long lifespan by the inclusion of at least one functionalized polycyclic aromatic hydrocarbon compound among compounds represented by Formulae 1 to 7.

The functionalized polycyclic aromatic hydrocarbon compound represented by at least one of Formulae 1 to 7 may be used between a pair of electrodes of the organic light-emitting device. For example, the functionalized polycyclic aromatic hydrocarbon compound may be included in at least one of an emission layer, a hole transport region (for example, including at least one of a hole injection layer, a hole transport layer, and an electron blocking layer) between the first electrode and the emission layer, and an electron transport region (for example, at least one of a hole blocking layer, an electron transport layer, and an electron injection layer) between the emission layer and the second electrode. For example, the functionalized polycyclic aromatic hydrocarbon compound represented by at least one of Formulae 1 to 7 may be included in the emission layer. In this case, the emission layer may further include a dopant, and the functionalized polycyclic aromatic hydrocarbon compound included in the emission layer may act as a host. The emission layer may be a green emission layer emitting green light, and the dopant may be a phosphorescent dopant.

As used herein, the expression "(an organic layer) includes at least one functionalized polycyclic aromatic hydrocarbon compound" may be construed as meaning that the organic layer includes one functionalized polycyclic aromatic hydrocarbon compound represented by one of Formulae 1 to 7 or two or more different functionalized polycyclic aromatic hydrocarbon compounds represented by Formulae 1 to 7.

For example, the organic layer may include one of the functionalized polycyclic aromatic hydrocarbon compounds represented by Formulae 1 to 7, alone. In this case, the functionalized polycyclic aromatic hydrocarbon compound may be present in the emission layer of the organic light-emitting device. In other embodiments, the organic layer may include two or more of the functionalized polycyclic aromatic hydrocarbon compounds represented by Formulae 1 to 7. In this case, each of the functionalized polycyclic aromatic hydrocarbon compound may be present in the same layer (for example, all of compounds 1 are in the emission layer) or may be present in different layers.

For example, the first electrode may be an anode, the second electrode may be a cathode, the organic layer may include: i) a hole transport region interposed between the first electrode and the emission layer and including at least one of a hole injection layer, a hole transport layer, and an electron blocking layer; and ii) an electron transport region interposed between the emission layer and the second electrode and including at least one of a hole blocking layer, an electron transport layer and an electron injection layer.

The term "organic layer" as used herein refers to a single layer and/or a plurality of layers between the first electrode and the second electrode of the organic light-emitting device. The "organic layer" may include, in addition to an organic compound, an organometallic complex including metal.

Figure 14:
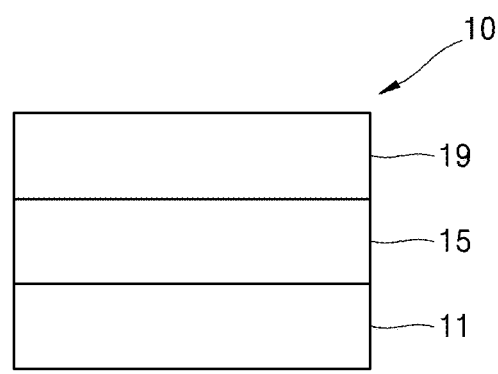
FIG. 14 is a schematic cross-sectional view of an organic light-emitting device according to an example.

FIG. 14 is a schematic cross-sectional view of an organic light-emitting device 10 according to an embodiment. Hereinafter, the structure of the organic light-emitting device according to an embodiment and a method of manufacturing the same will be described with reference to FIG. 14. The organic light-emitting device 10 may have a structure in which a first electrode 11, an organic layer 15, and a second electrode 19 which are sequentially stacked.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water resistance.

In one or more embodiments, the first electrode 11 may be formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode 11 may be indium tin oxide (ITO), indium zinc oxide (IZO), tin oxide ($SnO_2$), or zinc oxide (ZnO). In one or more embodiments, the material for forming the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layered structure or a multi-layered structure including two or more layers.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In one or more embodiments, the hole transport region may have a hole injection layer/hole transport layer structure or a hole injection layer/hole transport layer/electron blocking layer structure, which are sequentially stacked in this stated order from the first electrode 11.

When the hole transport region includes a hole injection layer (HIL), the hole injection layer may be formed on the first electrode 11 by using one or more suitable methods, for example, vacuum deposition, spin coating, casting, and/or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100° C. to about 500° C., a vacuum pressure of about $10^{-8}$ to about $10^{-3}$ torr, and a deposition rate of about 0.01 Å/sec to about 100 Å/sec. However, the deposition conditions are not limited thereto.

When the hole injection layer is formed using spin coating, the coating conditions may vary according to the compound that is used to form the hole injection layer, and the desired structure and thermal properties of the hole injection layer to be formed. For example, the coating rate may be in the range of about 2,000 rpm to about 5,000 rpm, and a temperature at which heat treatment is performed to remove a solvent after coating may be in the range of about 80° C. to about 200° C. However, the coating conditions are not limited thereto.

Conditions for forming a hole transport layer and an electron blocking layer may be understood by referring to the conditions for forming the hole injection layer.

The hole transport region may include at least one of m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), a compound represented by Formula 8, and a compound represented by Formula 9.

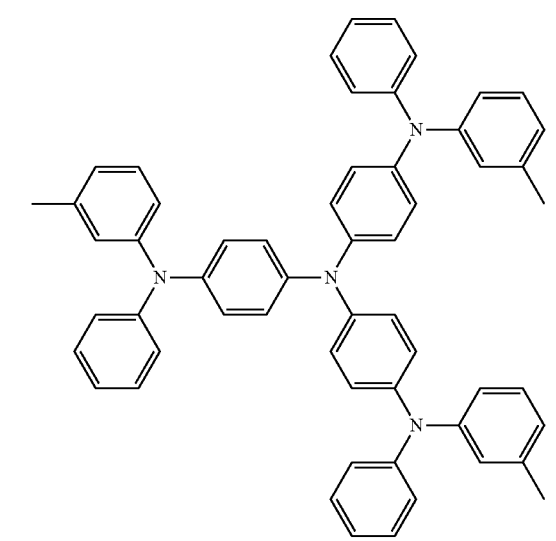
m-MTDATA
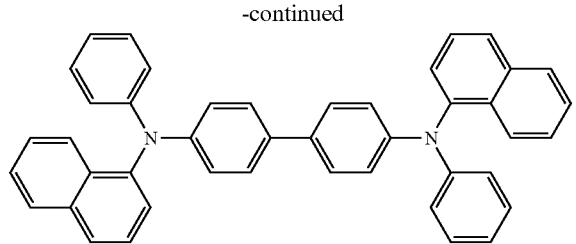
NPB
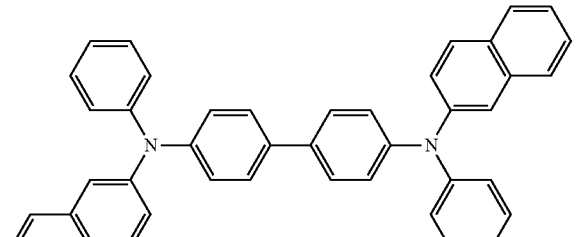
β-NPB
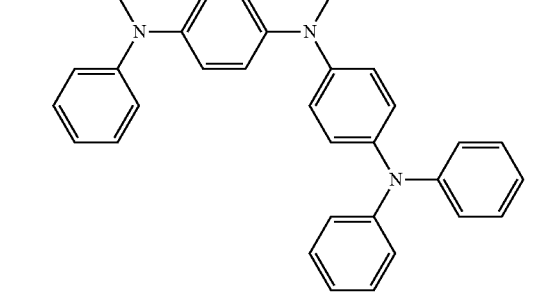
TPD
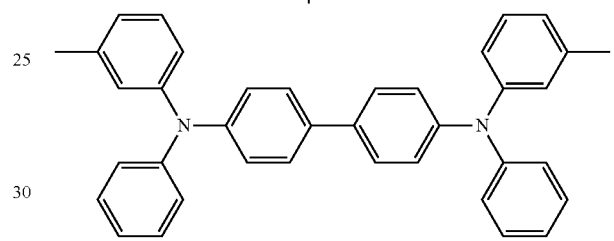
TDATA
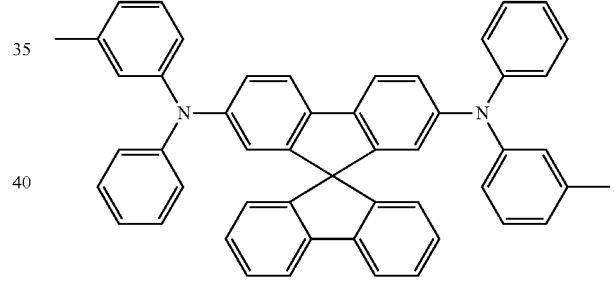
Spiro-TPD
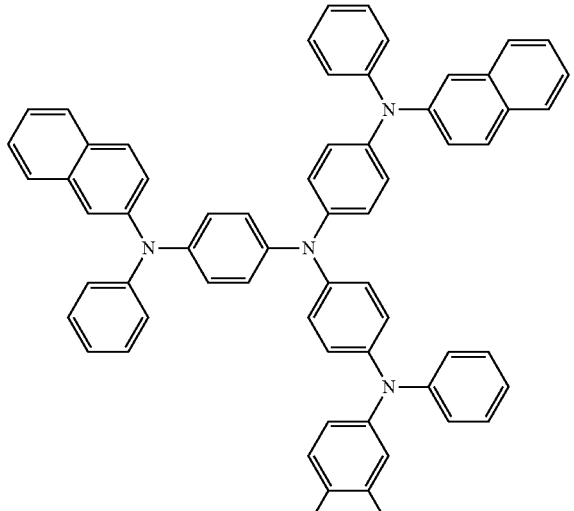
2-TNATA
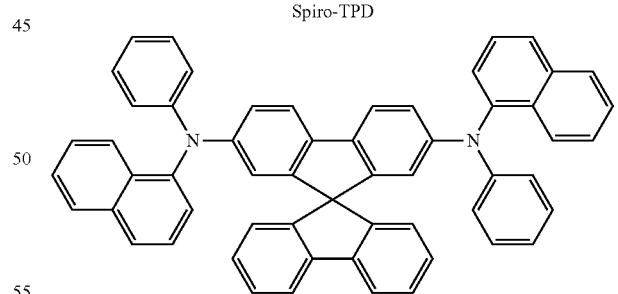
Spiro-NPD
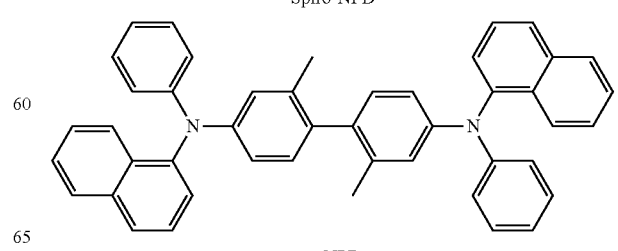
α-NPB -continued

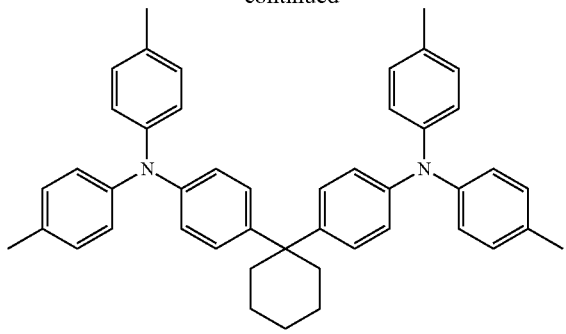

TAPC

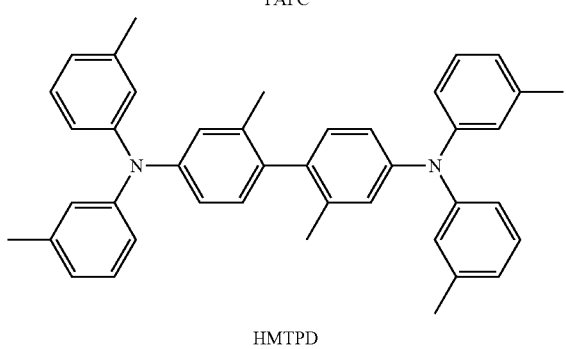

HMTPD

<Formula 8>

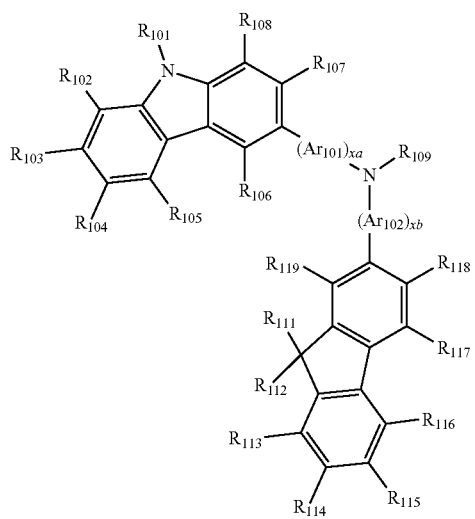

<Formula 9>

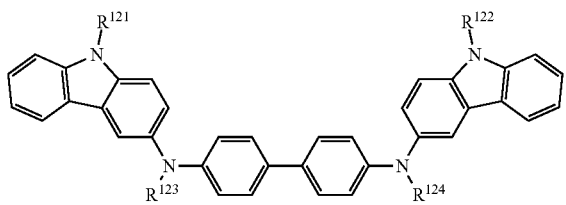

In Formula 8, $Ar_{101}$ and $Ar_{102}$ may each independently be selected from:

a phenylene group, a pentalenylene group, an indenylene group, a naphthylene group, an azulenylene group, a heptalenylene group, an acenaphthylene group, a fluo-renylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one of deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group.

In Formula 8, xa and xb may each independently be an integer from 0 to 5, or 0, 1 or 2. For example, xa may be 1 and xb may be 0, but xa and xb are not limited thereto.

In Formulae 8 and 9, $R_{101}$ to $R_{108}$, $R_{111}$ to $R_{119}$, and $R_{121}$ to $R_{124}$ may each independently be one of hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, and the like), or a $C_1$-$C_{10}$ alkoxy group (for example, a methoxy group, an ethoxy group, a propoxy group, a butoxy group, a pentoxy group, and the like);

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof;

a phenyl group, a naphthyl group, an anthracenyl group, a fluorenyl group, or a pyrenyl group; and a phenyl group, a naphthyl group, an anthracenyl group, a fluorenyl group, and a pyrenyl group, each substituted with at least one selected from deuterium, —F, —$C_1$, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group. However, embodiments of the present disclosure are not limited thereto.

In Formula 201, $R_{109}$ may be one of: a phenyl group, a naphthyl group, an anthracenyl group and a pyridinyl group; and a phenyl group, a naphthyl group, an anthracenyl group, and a pyridinyl group, each substituted with at least one of deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group.

In one embodiment, the compound represented by Formula 8 may be represented by Formula 8A. However, embodiments are not limited thereto.

<Formula 8A>

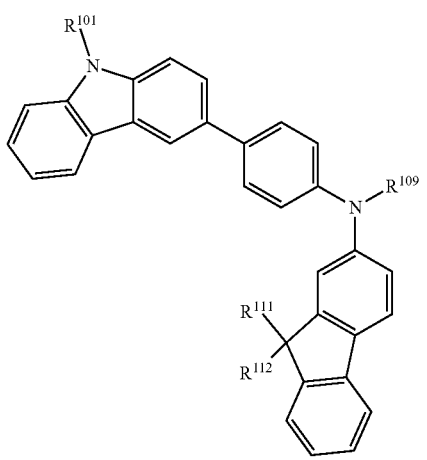

In Formula 8A, $R_{101}$, $R_{111}$, $R_{112}$ and $R_{109}$ are the same as described above.

For example, the compound represented by Formula 8, and the compound represented by Formula 8 may include compounds HT1 to HT20, but are not limited thereto.

HT1

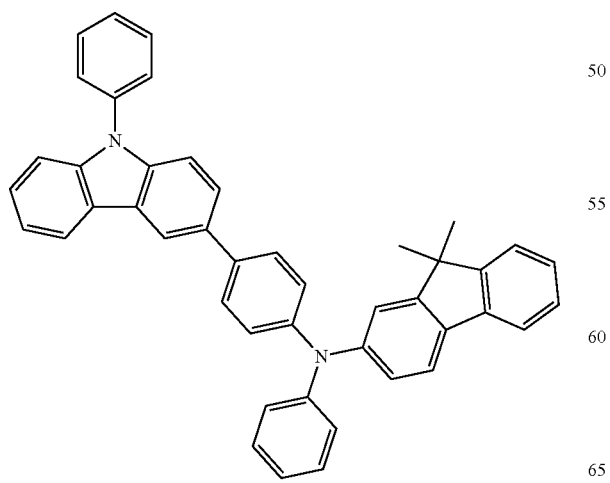

HT2

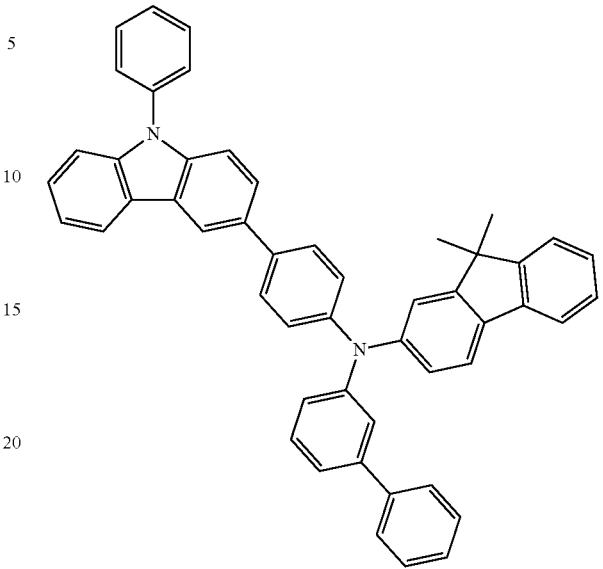

HT3

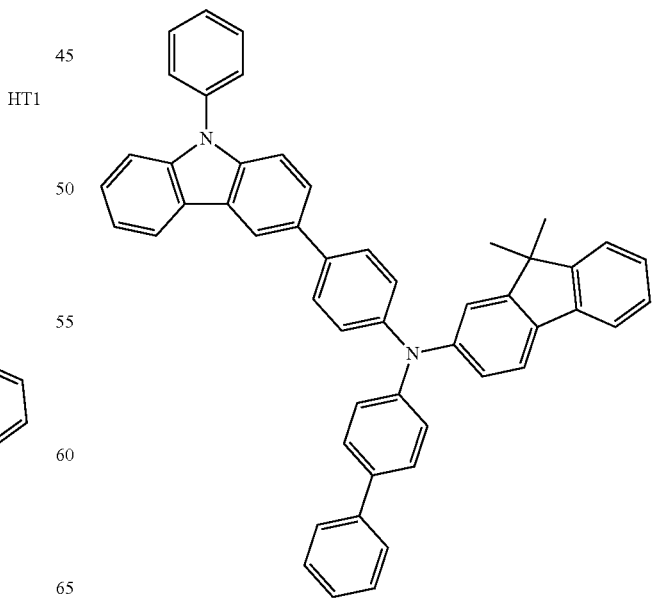

HT4
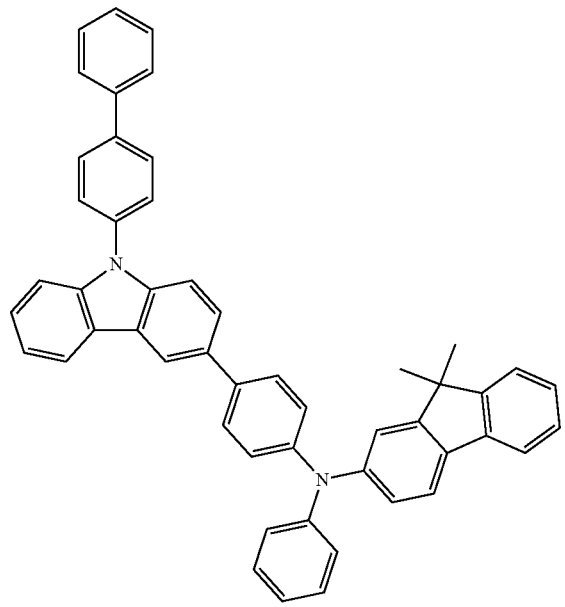
HT6
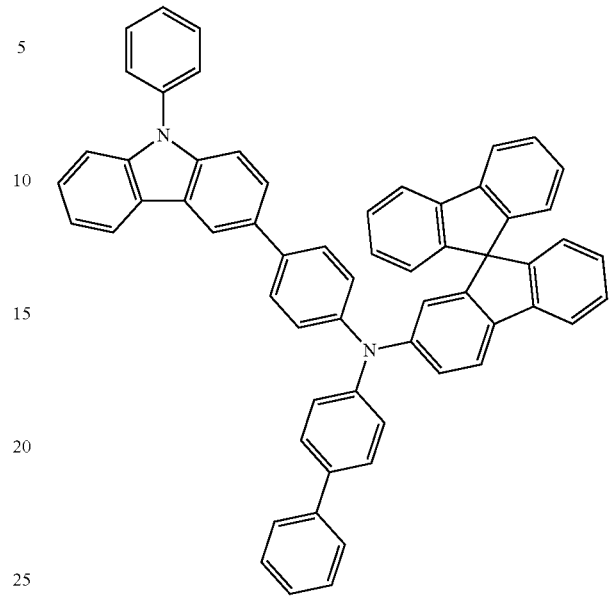
HT5
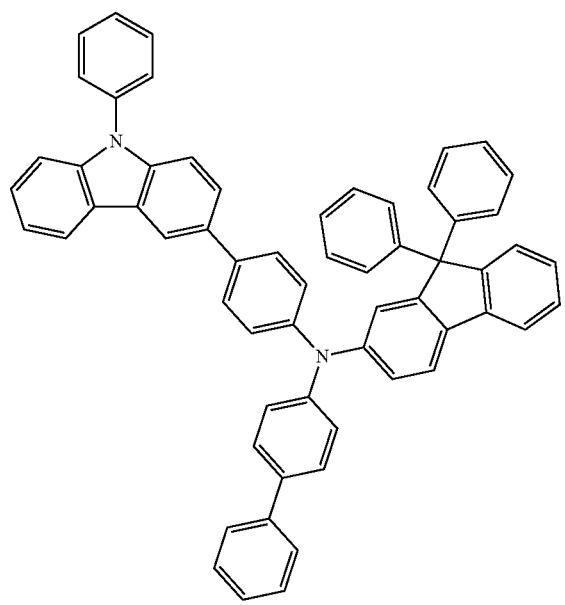
HT7

-continued
HT8
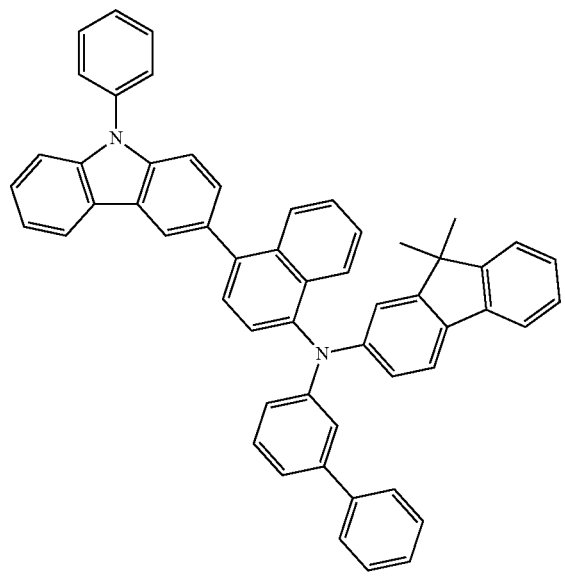
HT10
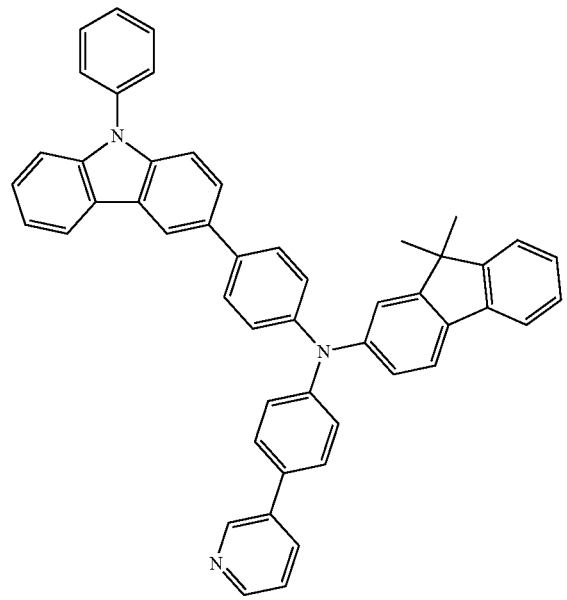
HT9
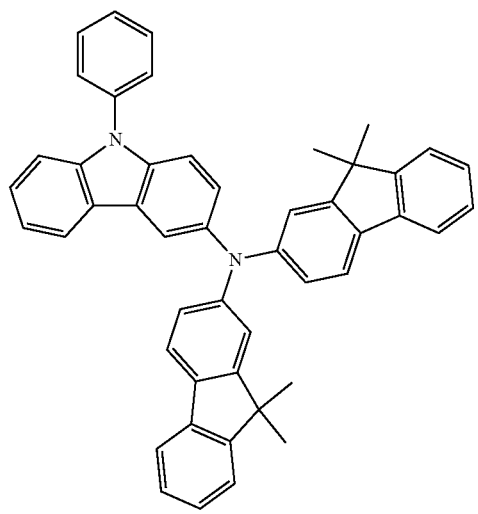
HT11
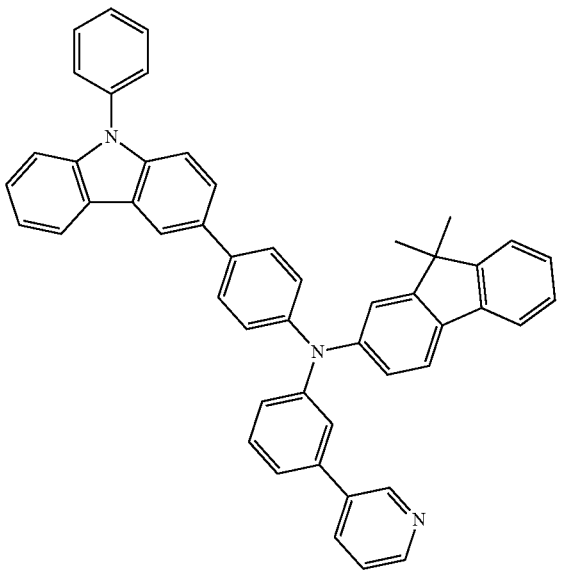

HT12
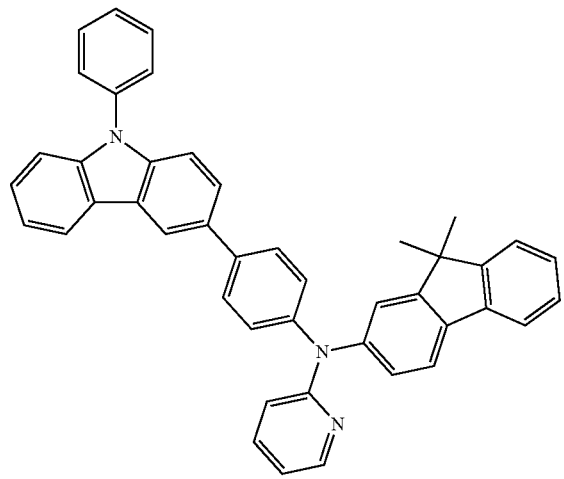
HT13
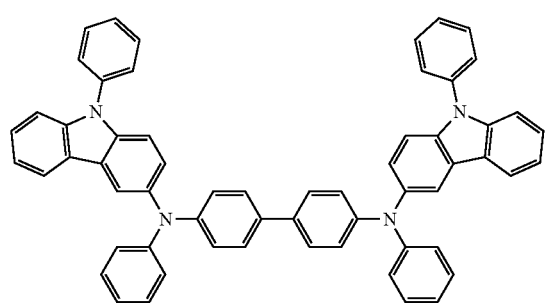
HT14
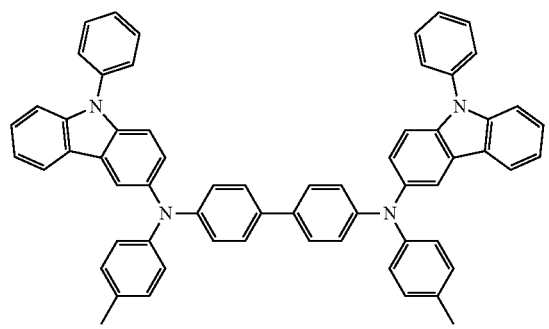
HT15
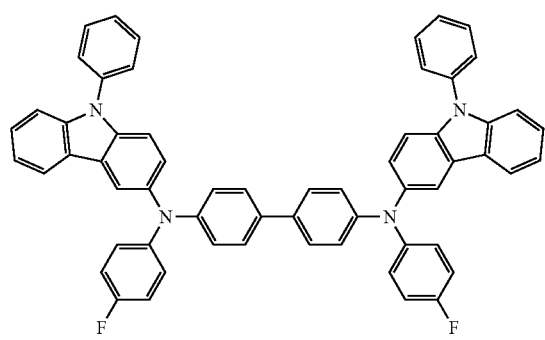
HT16
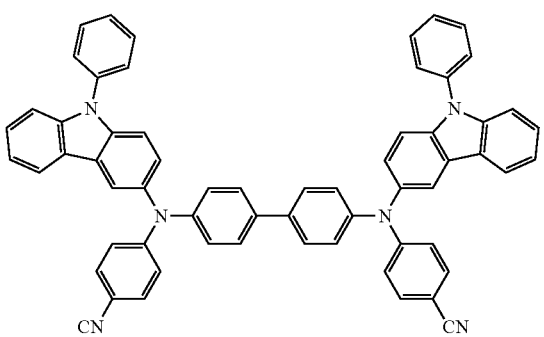
HT17
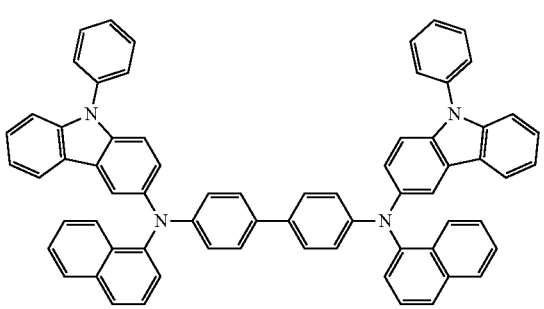
HT18
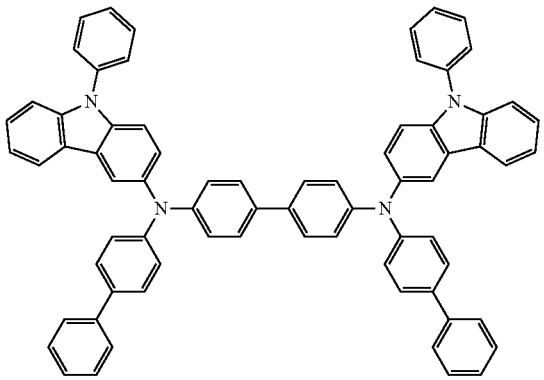
HT19
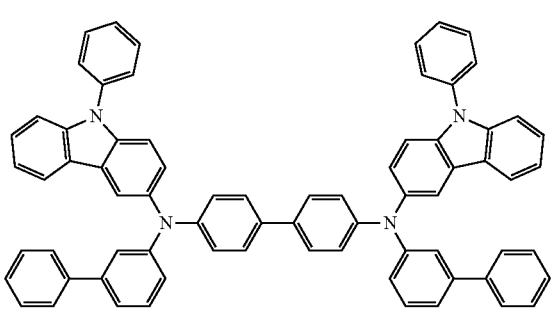

HT20

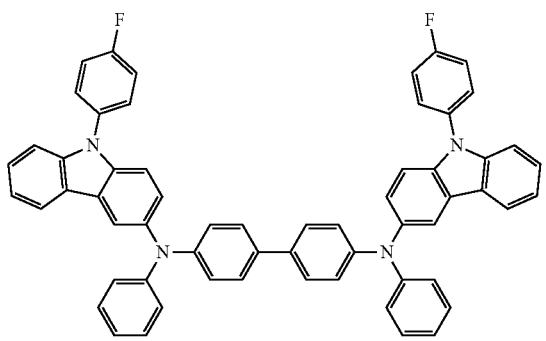

<F4-TCNQ>

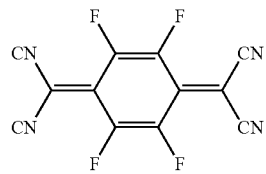

A thickness of the hole transport region may be in a range of about 100 Å to about 10,000 Å, for example, about 100 Å to about 1,000 Å. When the hole transport region includes a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generating material may be, for example, a p-dopant. The p-dopant may be one selected from a quinone derivative, a metal oxide, and a cyano group-containing compound, but embodiments of the present disclosure are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a cyano group-containing compound, such as Compound HT-D1, but are not limited thereto.

The hole transport region may include a buffer layer.

Also, the buffer layer may compensate for an optical resonance distance according to a wavelength of light emitted from the emission layer, and thus, efficiency of a formed organic light-emitting device may be improved.

Then, an emission layer may be formed on the hole transport region by vacuum deposition, spin coating, casting, LB deposition, or the like. When the emission layer is formed by vacuum deposition or spin coating, the deposition or coating conditions may be similar to those applied in forming the hole injection layer although the deposition or coating conditions may vary according to a compound that is used to form the emission layer.

The emission layer may include a host and a dopant. The host may include at least one of the one or more functionalized polycyclic aromatic hydrocarbon compounds represented by Formula 1.

The host may include, in addition to the functionalized polycyclic aromatic hydrocarbon compound represented by Formula 1, at least one of TPBi, TBADN, ADN (referred to also as "DNA"), CBP, CDBP, and TCP.

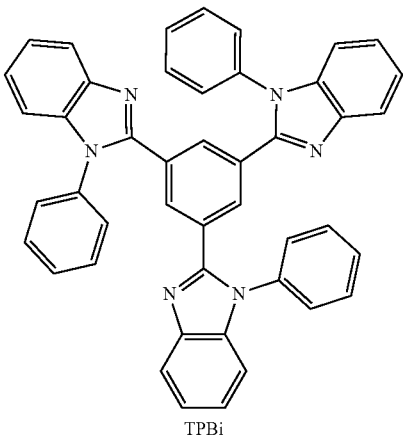

TPBi

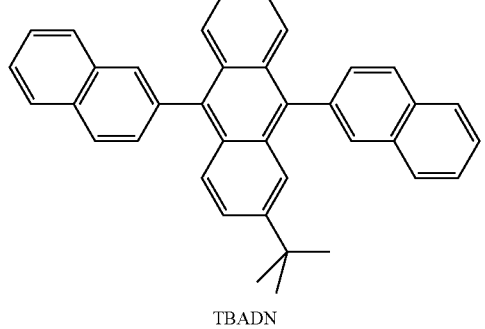

TBADN

<Compound HT-D1>

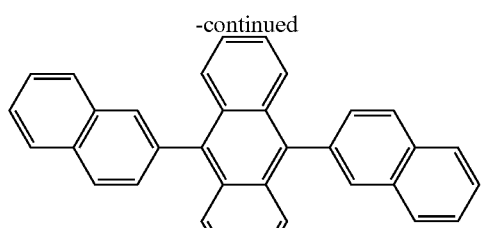

ADN

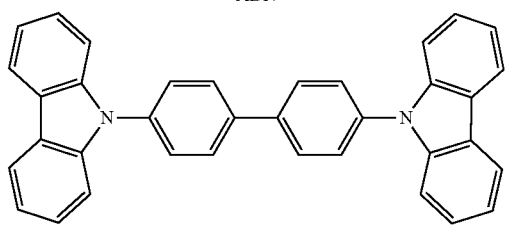

CBP

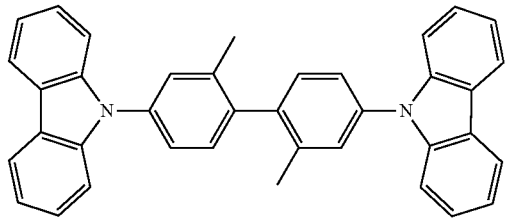

CDBP

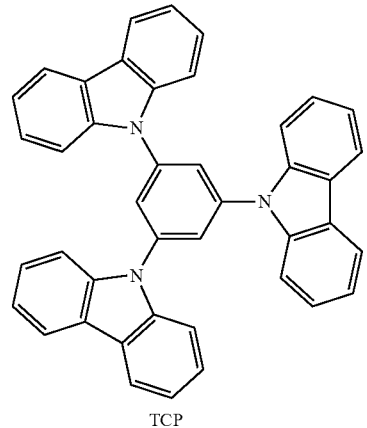

TCP

When the organic light-emitting device is a full-color organic light-emitting device, the emission layer may be patterned into a red emission layer, a green emission layer, and a blue emission layer. In one or more embodiments, due to a stacked structure including a red emission layer, a green emission layer, and/or a blue emission layer, the emission layer may emit white light. A host of the red emission layer, the green emission layer, and the blue emission layer may include the functionalized polycyclic aromatic hydrocarbon compound represented by Formula 1. In one embodiment, the host of the green emission layer may include at least one of the functionalized polycyclic aromatic hydrocarbon compounds represented by Formulae 1 to 7.

A dopant of the emission layer may include a fluorescent dopant emitting light according to a fluorescent emission mechanism, or a phosphorescent dopant emitting light according to a phosphorescent emission mechanism.

In one embodiment, the emission layer may include a host including at least one of the functionalized polycyclic aromatic hydrocarbon compounds represented by Formulae 1 to 7, and a phosphorescent dopant. The phosphorescent dopant may include an organometallic complex including a transition metal (for example, iridium (Ir), platinum (Pt), osmium (Os), rhodium (Rh), and the like).

The phosphorescent dopant may include an organometallic compound represented by Formula 10.

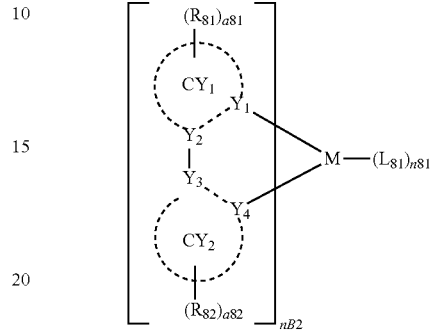

<Formula 10>

In Formula 10,

M may be selected from iridium (Ir), platinum (Pt), osmium (Os), titanium (Ti), zirconium (Zr), hafnium (Hf), europium (Eu), terbium (Tb), and thulium (Tm);

$Y_1$ to $Y_4$ may each independently be carbon (C) or nitrogen (N);

$Y_1$ and $Y_2$ may be linked to each other via a single bond or a double bond, and $Y_3$ and $Y_4$ may be linked to each other via a single bond or a double bond;

$CY_1$ and $CY_2$ may each independently be selected from a benzene, a naphthalene, a fluorene, a spiro-fluorene, an indene, a pyrrole, a thiophene, a furan, an imidazole, a pyrazole, a thiazole, an isothiazole, an oxazole, an isoxazole, a pyridine, a pyrazine, a pyrimidine, a pyridazine, a quinoline, an isoquinoline, a benzoquinoline, a quinoxaline, a quinazoline, a carbazole, a benzimidazole, a benzofuran, a benzothiophene, an isobenzothiophene, a benzoxazole, an isobenzoxazole, a triazole, a tetrazole, an oxadiazole, a triazine, a dibenzofuran, and a dibenzothiophene, and optionally, $CY_1$ $CY_2$ may be linked to each other via a single bond or an organic linking group;

$R_{81}$ and $R_{82}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —N(Q₁)(Q₂), —Si(Q₃)(Q₄)(Q₅), and —B(Q₆)(Q₇);

$a_{81}$ and $a_{82}$ may each independently be an integer selected from 1 to 5;

$n_{81}$ may be an integer selected from 0 to 4;

$n_{82}$ may be 1, 2 or 3;

$L_{81}$ may be selected from a monovalent organic ligand, a divalent organic ligand, and a trivalent organic ligand;

In Formula 10, the bond between $Y_1$ and $Y_2$ and the bond between $Y_3$ and $Y_4$ may each independently be a single bond or a double bond.

$R_{81}$ and $R_{82}$ may each independently be the same as defined in connection with $R_5$ herein.

The phosphorescent dopant may include at least one of Compounds PD1 to PD74, but is not limited thereto.

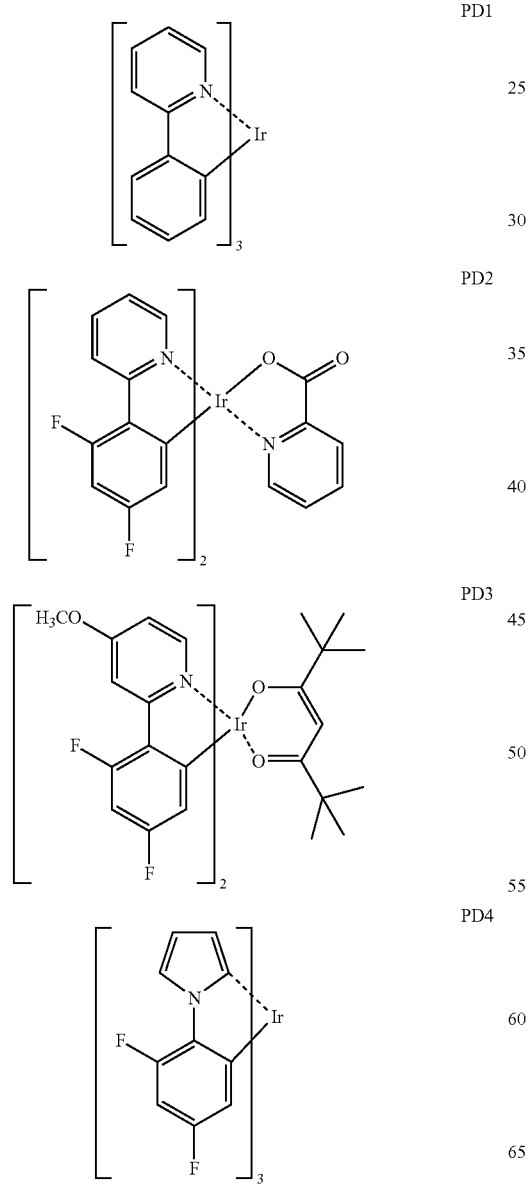

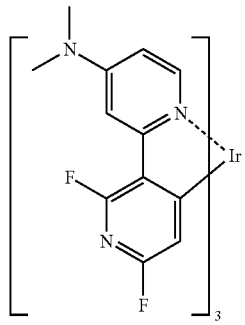

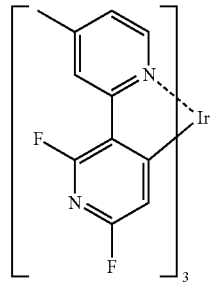

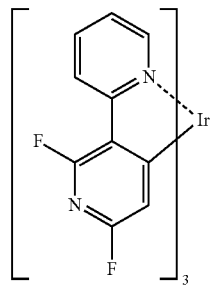

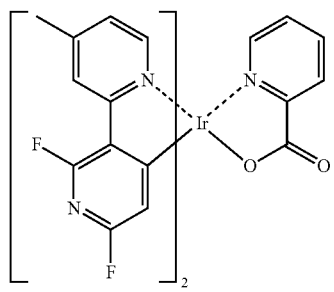

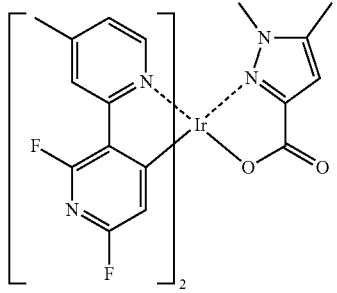

-continued
PD10
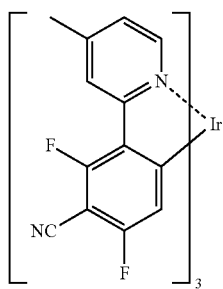
PD11
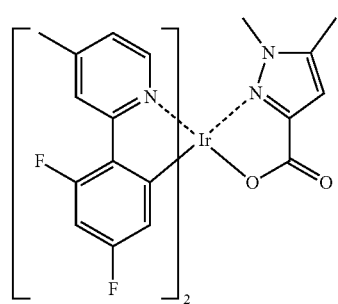
PD12
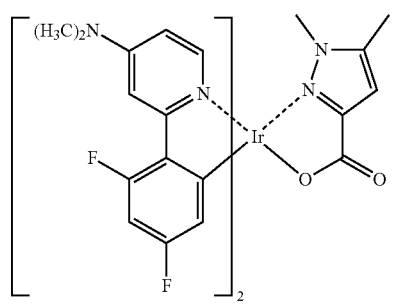
PD13
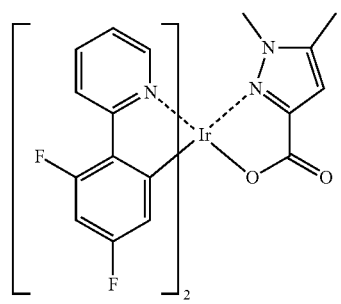
PD14
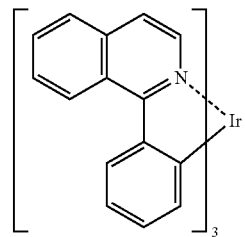
-continued
PD15
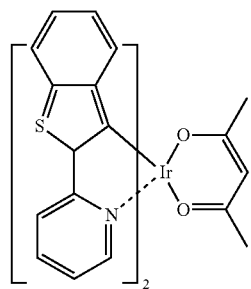
PD16
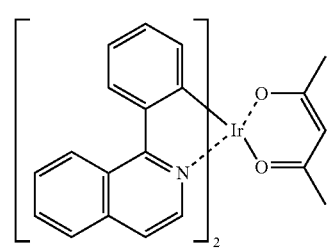
PD17
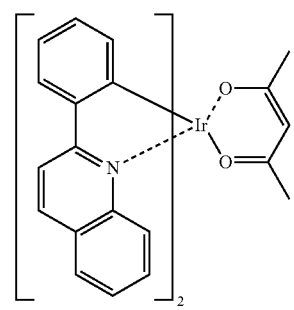
PD18
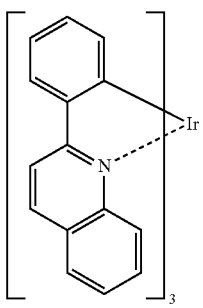
PD19
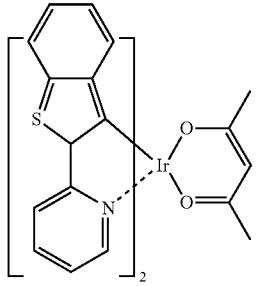

PD20
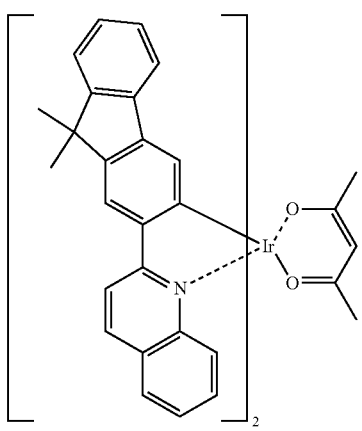
PD21
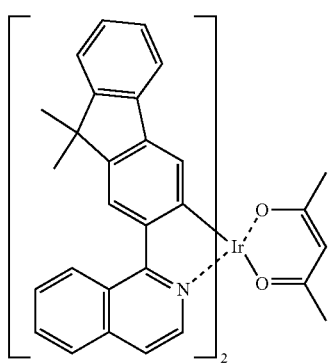
PD22
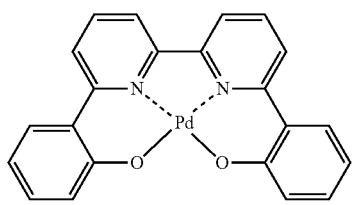
PD23
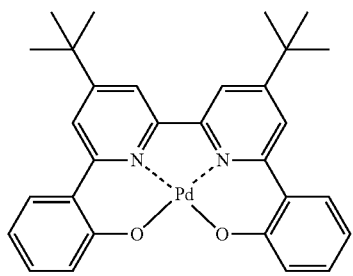
PD24
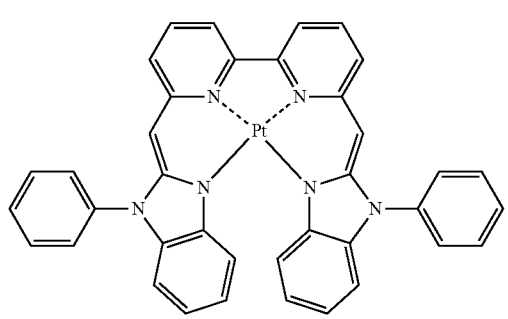
PD25
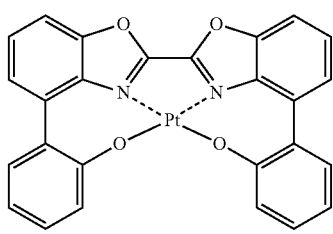
PD26
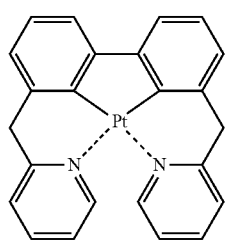
PD27
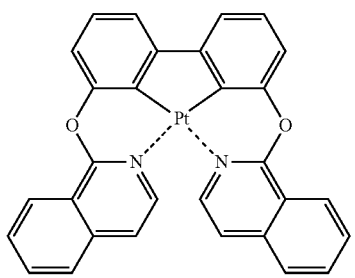
PD28
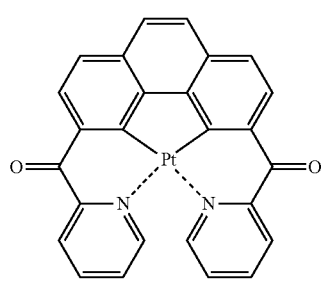
PD29
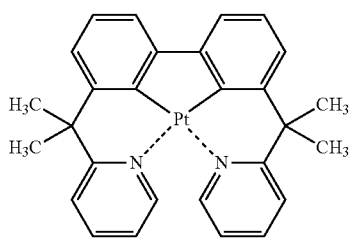
PD30
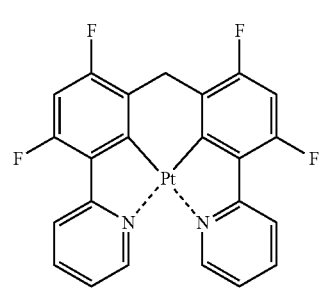

PD31
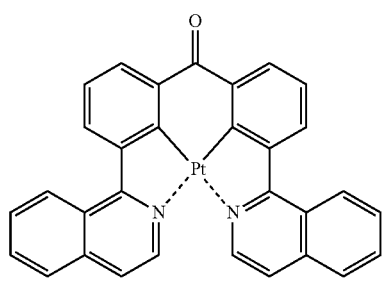
PD36
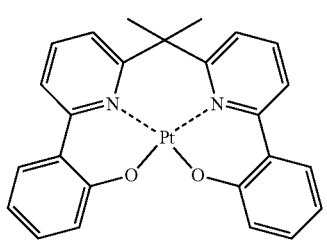
PD32
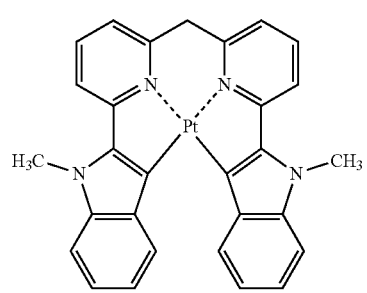
PD37
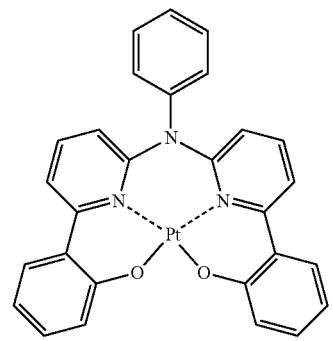
PD33
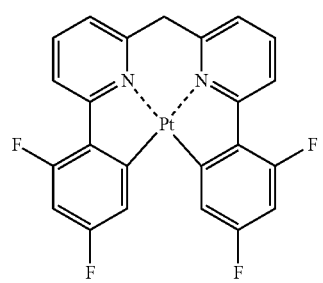
PD38
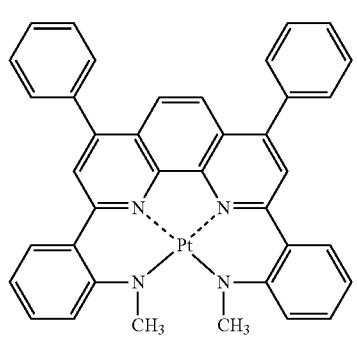
PD34
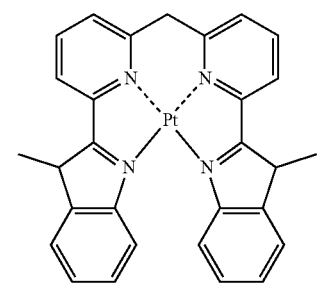
PD39
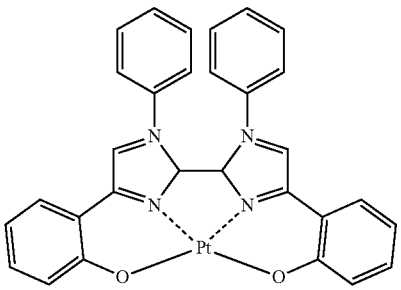
PD35
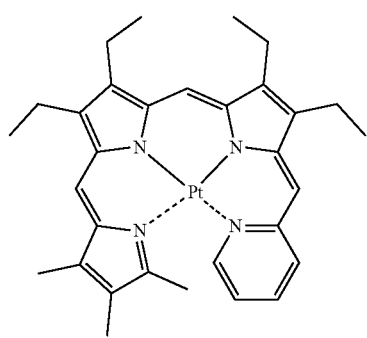
PD40
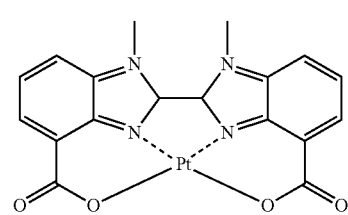
PD41
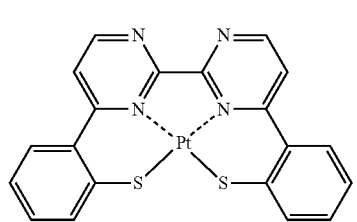

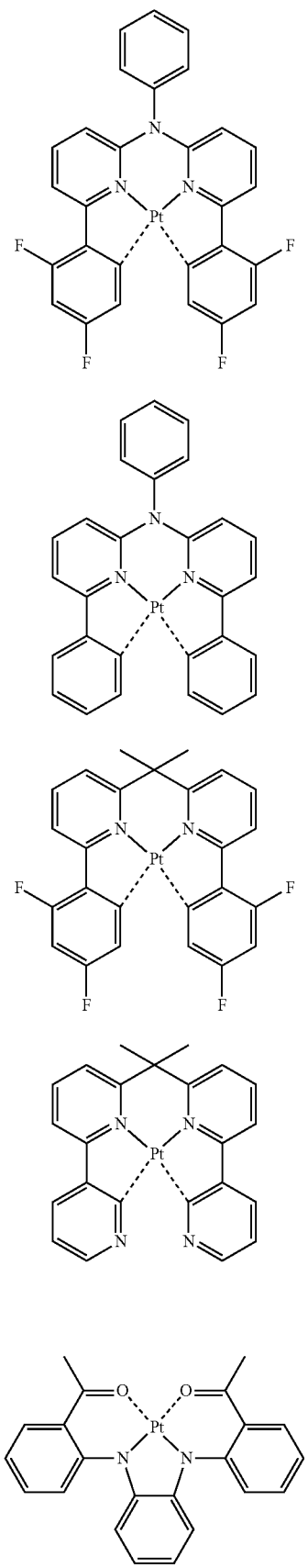

PD53
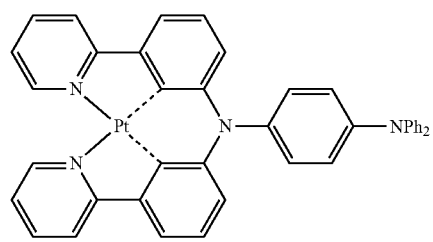
PD54
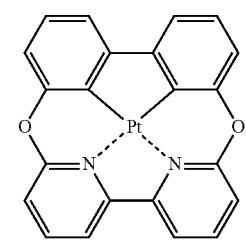
PD55
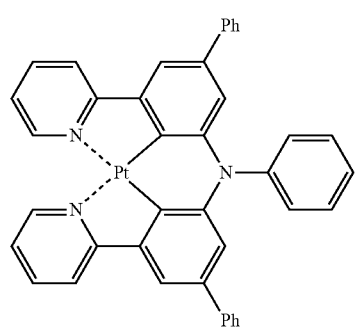
PD56
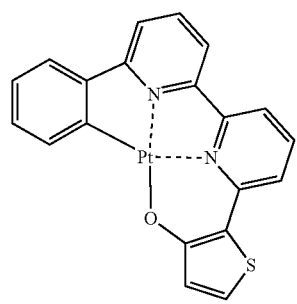
PD57
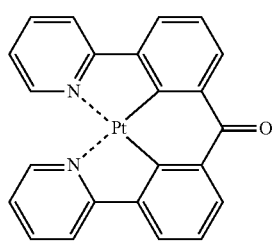
PD58
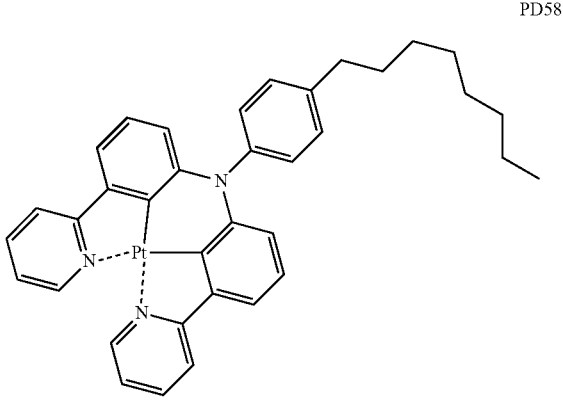
PD59
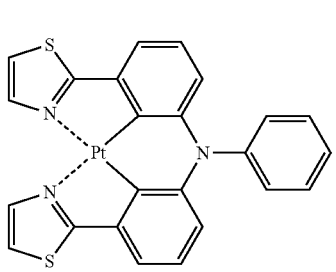
PD60
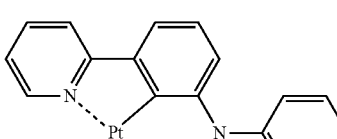
PD61
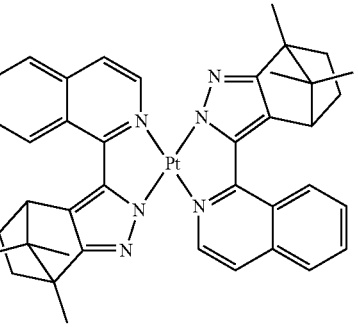
PD62
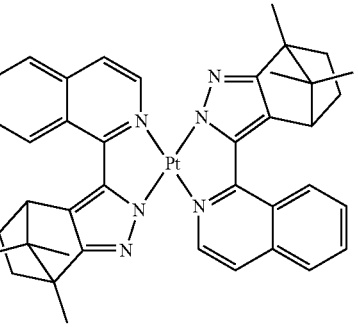

-continued
PD63
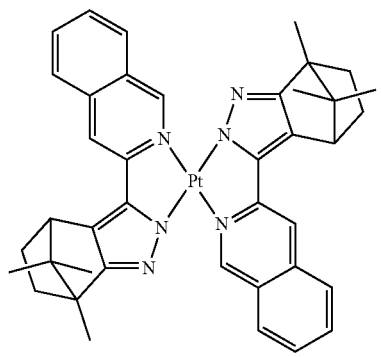
PD64
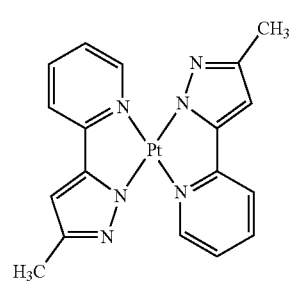
PD65
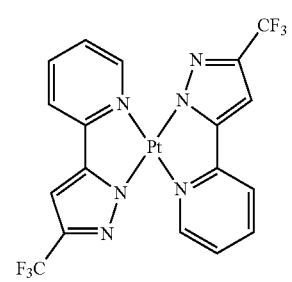
PD66
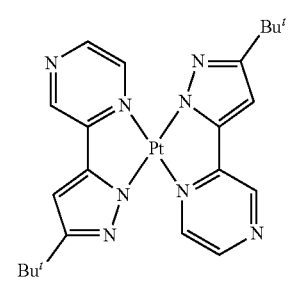
PD67
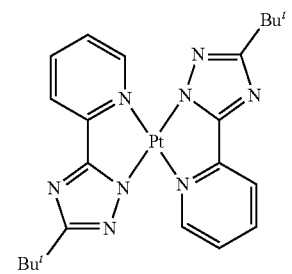
-continued
PD68
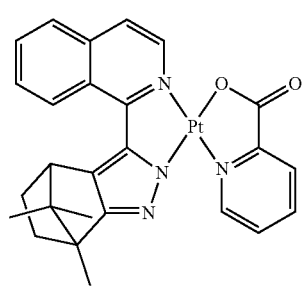
PD69
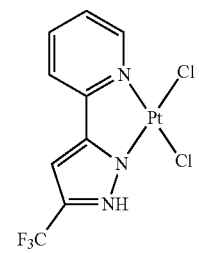
PD70
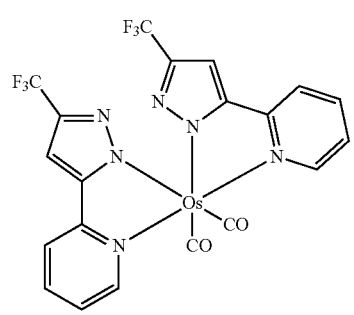
PD71
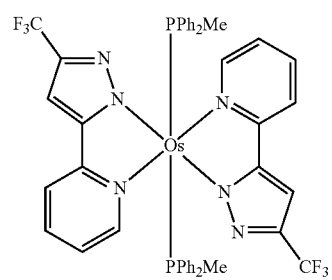
PD72
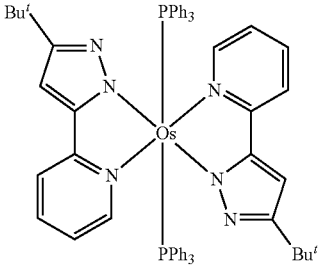

PD73
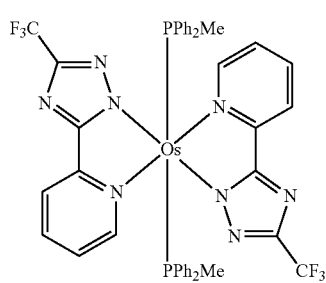
PD74
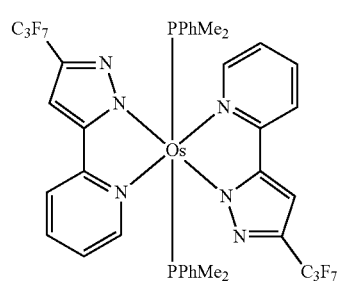
In one or more embodiments, the phosphorescent dopant may include PtOEP or Compound PhGD as below.
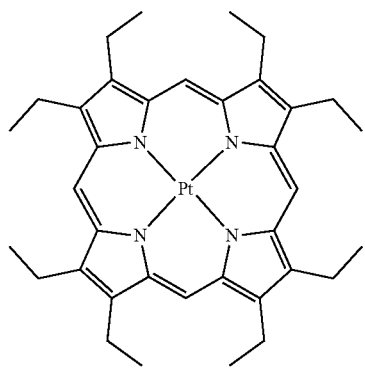
PtOEP
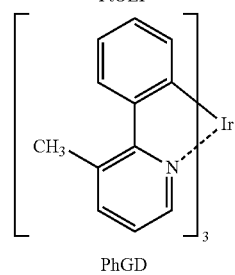
PhGD
The fluorescent dopant may include at least one of DPVBi, DPAVBi, TBPe, DCM, DCJTB, Coumarin 6, and C545T as below.
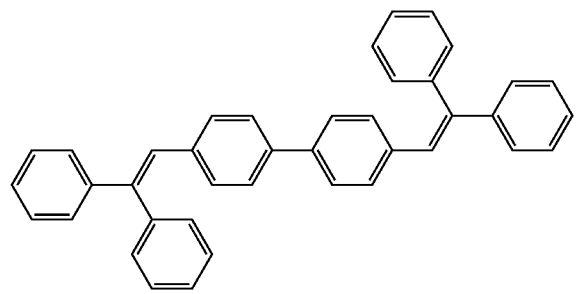
DPVBi
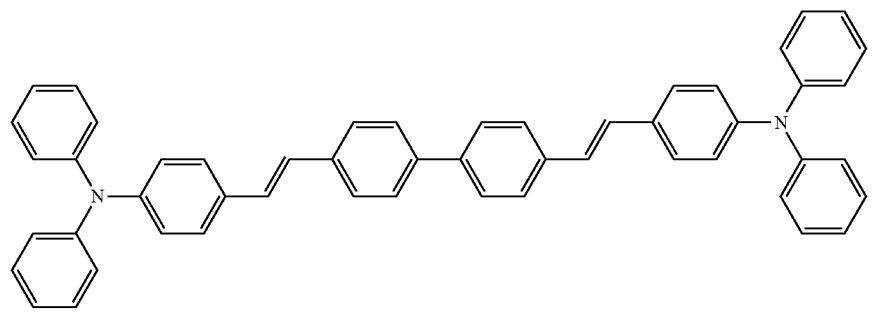
DPAVBi

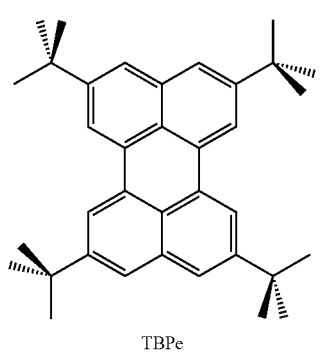
TBPe

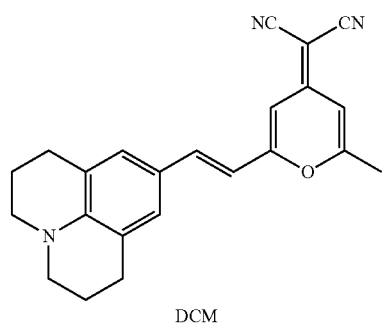
DCM

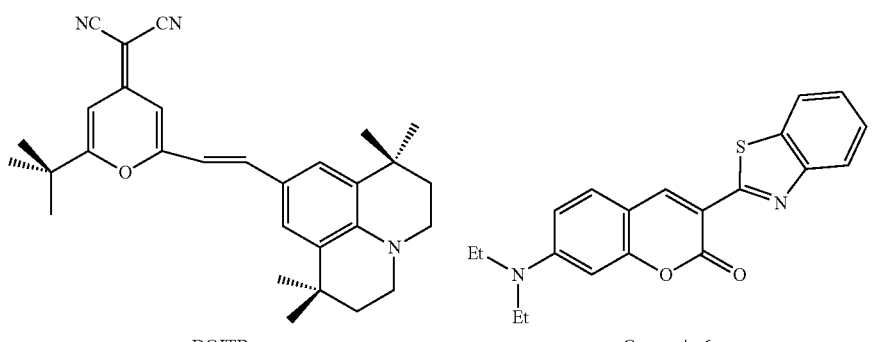

DCJTB

Coumarin 6

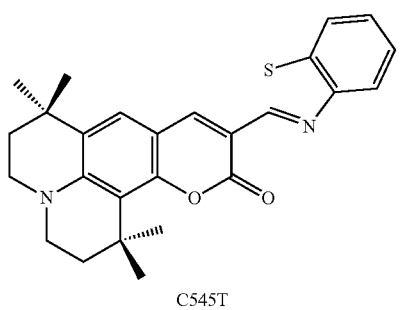
C545T

When the emission layer includes a host and a dopant, an amount of the dopant may be in a range of about 0.01 parts to about 20 parts by weight with respect to 100 parts by weight of the host, but embodiments of the present disclosure are not limited thereto A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one of a hole blocking layer, an electron transport layer, and an electron injection layer.

For example, the electron transport region may have an electron transport layer, a hole blocking layer/electron transport layer/electron injection layer structure, or an electron transport layer/electron injection layer structure, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one of BCP and Bphen, but embodiments are not limited thereto.

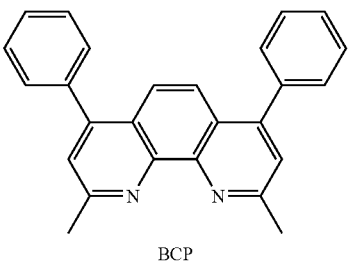
BCP

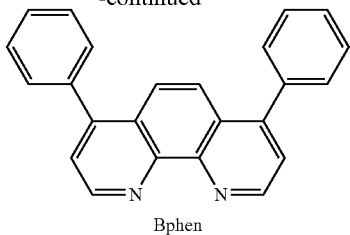

Bphen

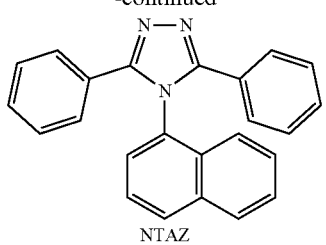

NTAZ

A thickness of the hole blocking layer may be in a range of about 20 Å to about 1,000 Å, for example, about 30 Å to about 300 Å. When the thickness of the hole blocking layer is within these ranges, the hole blocking layer may have excellent hole blocking characteristics without a substantial increase in driving voltage.

The electron transport layer may further include, in addition to the organometallic compound represented by Formula 1, at least one selected from BCP, Bphen, Alq$_3$, BAlq, TAZ, and NTAZ.

In one or more embodiments, the electron transport layer may include at least one of Compounds ET1 and ET2, but embodiments of the present disclosure are not limited thereto

ET1

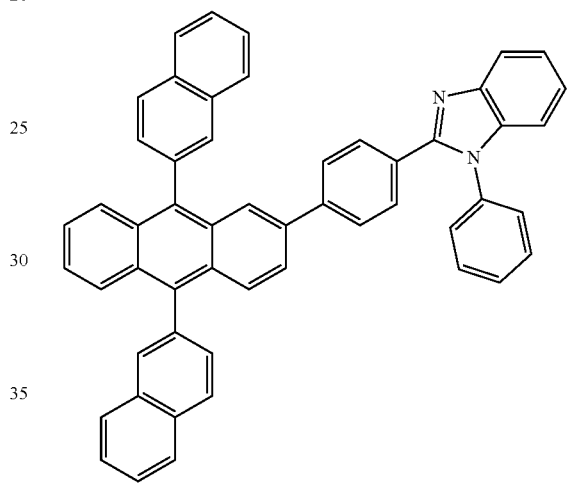

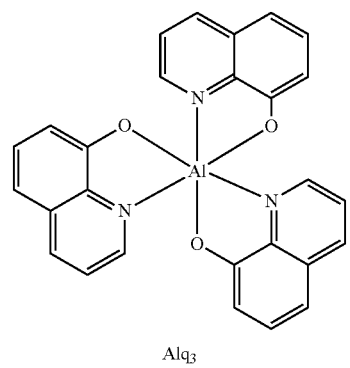

Alq$_3$

ET2

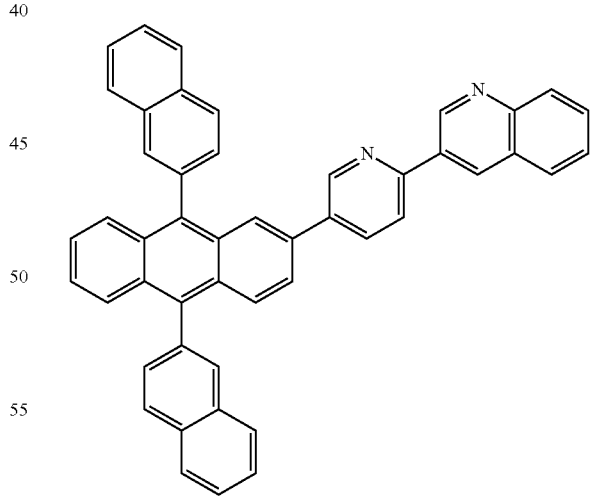

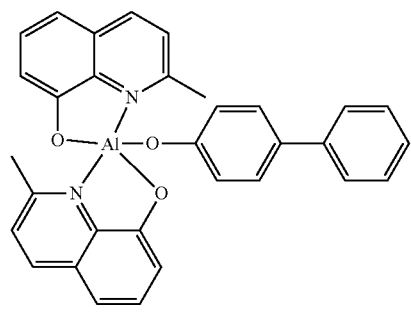

BAlq

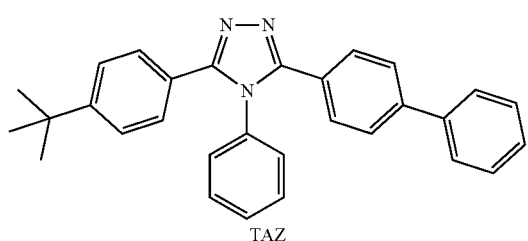

TAZ

A thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

The electron transport layer may further include, in addition to the materials described above, a metal-containing material.

The metal-containing material may include a Li complex. The Li complex may include, for example, Compound ET-D1 (lithium quinolate, LiQ) or ET-D2.

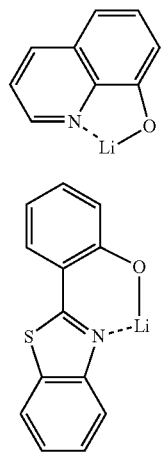

ET-D1

ET-D2

The electron transport region may include an electron injection layer that promotes flow of electrons from the second electrode 19 therein.

The electron injection layer may include at least one selected from LiF, a NaCl, CsF, $Li_2O$, and BaO.

A thickness of the electron injection layer may be in a range of about 1 Å to about 100 Å, for example, about 3 Å to about 90 Å. When the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be metal, an alloy, an electrically conductive compound, or a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as the material for forming the second electrode 19. To manufacture a top-emission type light-emitting device, a transmissive electrode formed using ITO or IZO may be used as the second electrode 19.

Hereinbefore, the organic light-emitting device has been described with reference to FIG. 20, but embodiments of the present disclosure are not limited thereto.

The term "$C_1$-$C_{60}$ alkyl group" as used herein refers to a linear or branched aliphatic hydrocarbon monovalent group having 1 to 60 carbon atoms, and examples thereof include a methyl group, an ethyl group, a propyl group, an isobutyl group, a sec-butyl group, a tert-butyl group, a pentyl group, an isoamyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by -$OA_{101}$ (wherein $A_{101}$ is the $C_1$-$C_{60}$ alkyl group), and examples thereof include a methoxy group, an ethoxy group, and an isopropyloxy group.

The term "$C_2$-$C_{60}$ alkenyl group" as used herein refers to a hydrocarbon group having at least one double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_2$-$C_{10}$ heterocycloalkyl group" as used herein refers to a monovalent saturated monocyclic group having at least one heteroatom selected from N, O, P, and S as a ring-forming atom and 2 to 10 carbon atoms, and non-limiting examples thereof include a tetrahydrofuranyl group, and a tetrahydrothiophenyl group. The term "$C_2$-$C_{10}$ heterocycloalkylene group" as used herein refers to a divalent group having the same structure as the $C_2$-$C_{10}$ heterocycloalkyl group.

The term "$C_3$-$C_{10}$ cycloalkenyl group" as used herein refers to a monovalent monocyclic group that has 3 to 10 carbon atoms and at least one double bond in the ring thereof and no aromaticity, and non-limiting examples thereof include a cyclopentenyl group, a cyclohexenyl group, and a cycloheptenyl group. The term "$C_3$-$C_{10}$ cycloalkenylene group," used herein, refers to a divalent group having the same structure as the $C_3$-$C_{10}$ cycloalkenyl group.

The term "$C_2$-$C_{10}$ heterocycloalkenyl group" as used herein refers to a monovalent monocyclic group that has at least one heteroatom selected from N, O, P, and S as a ring-forming atom, 2 to 10 carbon atoms, and at least one double bond in its ring. Examples of the $C_2$-$C_{10}$ heterocycloalkenyl group are a 2,3-dihydrofuranyl group, and a 2,3-dihydrothiophenyl group. The term "$C_2$-$C_{10}$ heterocycloalkenylene group," used herein, refers to a divalent group having the same structure as the $C_2$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_2$-$C_{60}$ heteroaryl group" as used herein refers to a monovalent group having a cyclic aromatic system that has at least one heteroatom selected from N, O, P, and S as a ring-forming atom, in addition to 2 to 60 carbon atoms. The term "$C_2$-$C_{60}$ heteroarylene group" as used herein refers to a divalent group having a cyclic aromatic system that has at least one heteroatom selected from N, O, P, and S as a ring-forming atom, in addition to 2 to 60 carbon atoms.

Examples of the $C_2$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl group and the $C_2$-$C_{60}$ heteroarylene group each include two or more rings, the rings may be fused to each other.

The term "$C_6$-$C_{60}$ aryloxy group" as used herein refers to -$OA_{102}$ (wherein $A_{102}$ is the $C_6$-$C_{60}$ aryl group), and the term "$C_6$-$C_{60}$ arylthio group" as used herein refers to -$SA_{103}$ (wherein $A_{103}$ is the $C_6$-$C_{60}$ aryl group).

The term "monovalent non-aromatic condensed polycyclic group" as used herein refers to a monovalent group having two or more rings condensed to each other, only carbon atoms (for example, the number of carbon atoms may be in a range of 8 to 60) as a ring-forming atom, and no aromaticity in its entire molecular structure. Non-limiting examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group having two or more rings condensed to each other, a heteroatom selected from N, O, P, and S, other than carbon atoms (for example, the number of carbon atoms may be in a range of 2 to 60), as a ring-forming atom, and no aromaticity in its entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

Hereinafter, a compound and an organic light-emitting device according to embodiments are described in detail with reference to synthesis examples and examples. However, the organic light-emitting device is not limited thereto. The wording "'B' was used instead of 'A'" used in describing synthesis examples means that a molar equivalent of 'A' was identical to a molar equivalent of 'B'.

One or more embodiments of the present disclosure will now be described in detail with reference to the following examples. However, these examples are only for illustrative purposes and are not intended to limit the scope of the one or more embodiments of the present disclosure.

Synthesis of Functionalized Polycyclic Aromatic Hydrocarbon Compound

Synthesis Example 1: Synthesis of Compound 1 (Py-P2

Compound 1 (Py-P2) was synthesized according to the following reaction scheme.

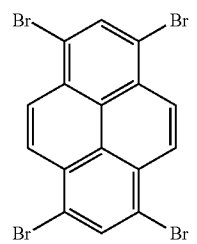

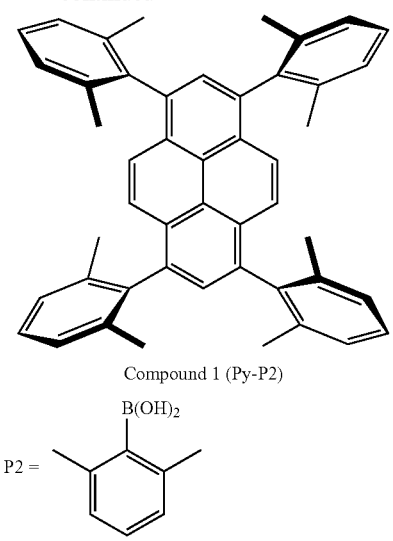

Compound 1 (Py-P2)

$P2 =$ (i) P2(5.0 equiv.), Pd(PPh$_3$)$_4$ (40 mol %), Cs$_2$CO$_3$ (5.0 equiv.), 1,4-dioxane, reflux, 1 d.

Tetrabromopyrene, dimethylphynyl boronic acid (5 equiv.), Pd(PPh$_3$)$_4$ (40 mol %), Cs$_2$CO$_3$ (5 equiv.), and 1,4-dioxane were put into a 500-mL round-bottom flask and heated in a nitrogen atmosphere under reflux for 24 hours. After filtration of solids crystallized by addition of 1000 mL of methanol to the resulting mixture, the filtered product was dissolved in monochlorobenzene and filtered using a silica gel/Celite. After removal of an appropriate amount of the organic solvent, the resulting product was recrystallized with methanol to yield Compound 1 (0.2 g, Yield: 49%).

Synthesis Example 2: Synthesis of Compound 2 (Coro-P2

Compound 2 (Coro-P2) was synthesized according to the following reaction scheme.

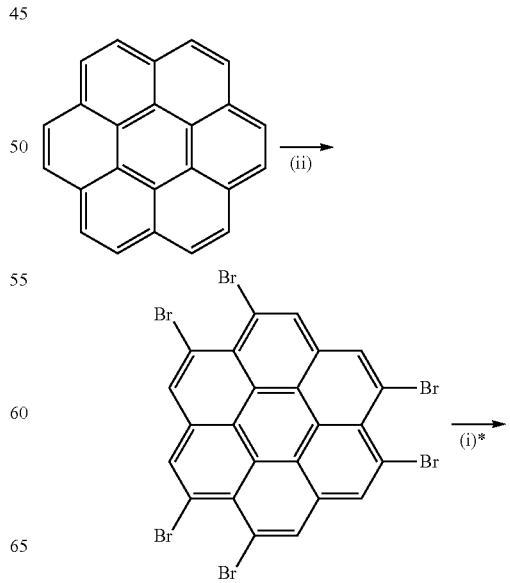

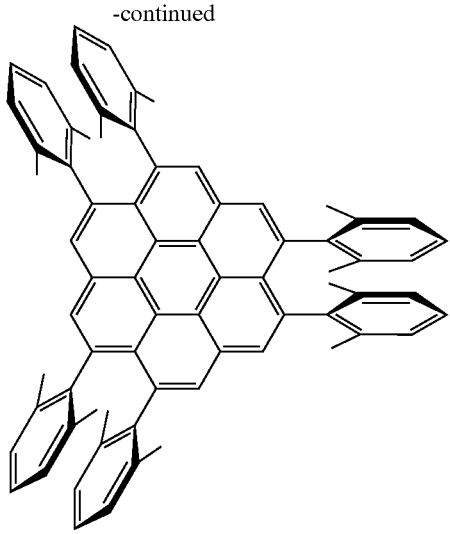

Compound 2 (Coro-P2)

(ii) Br$_2$ (12 equiv.), Fe powder (40 mol %), PhNO$_2$, 210° C., 12 h, (i)* P2(8.0 equiv.), Pd(PPh$_3$)$_4$ (40 mol %), Cs$_2$CO$_3$ (5.0 equiv.), 1,4-dioxane, reflux, 1 d.

Bromocoronene, dimethylphynyl boronic acid (2.5 equiv.), Pd(PPh$_3$)$_4$ (10 mol %), K$_2$CO$_3$ (5.0 equiv.), and PhMe/EtOH/H$_2$O (v/v/v=15/2/5) were put into a 500-mL round-bottom flask and heated in a nitrogen atmosphere at 60° C. under reflux for 24 hours. After filtration of solids crystallized by addition of 1000 mL of methanol to the resulting mixture, the filtered product was dissolved in monochlorobenzene and filtered using a silica gel/Celite. After removal of an appropriate amount of the organic solvent, the resulting product was recrystallized with methanol to yield Compound 2 (0.1 g, Yield: 10%).

Synthesis Example 3: Synthesis of Compound 3 (HBC-P2

Compound 3 (HBC-P2) was synthesized according to the following reaction scheme.

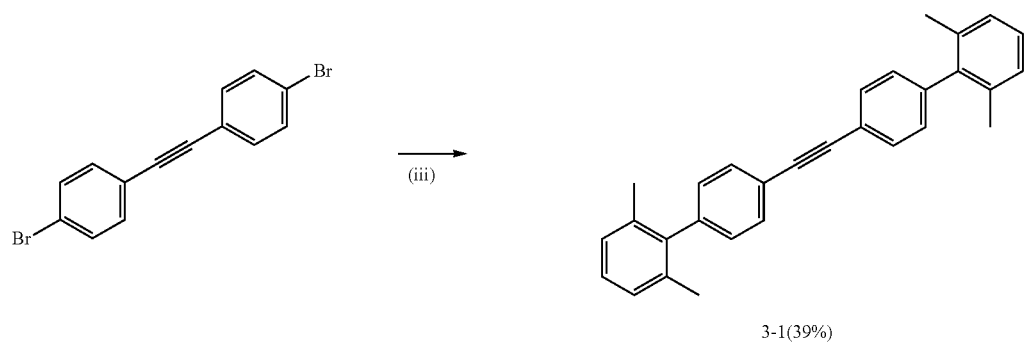

3-1(39%)

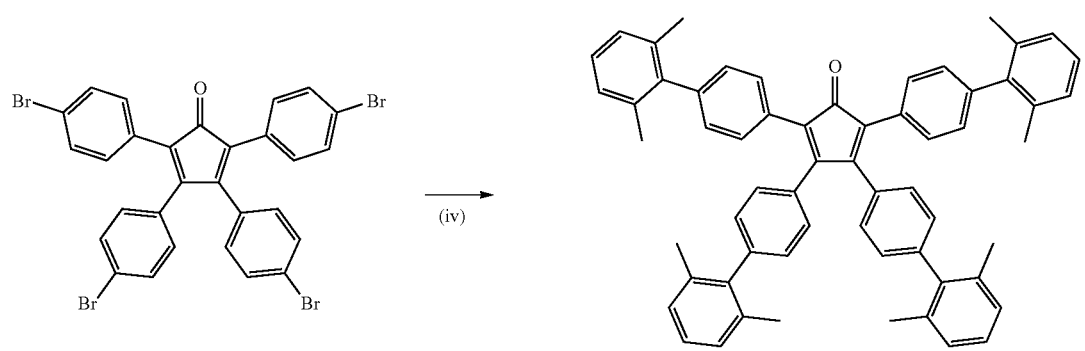

3-2(70%)

-continued
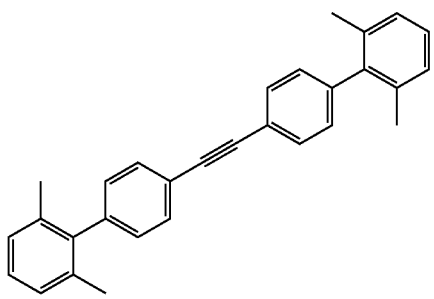
3-1(39%)
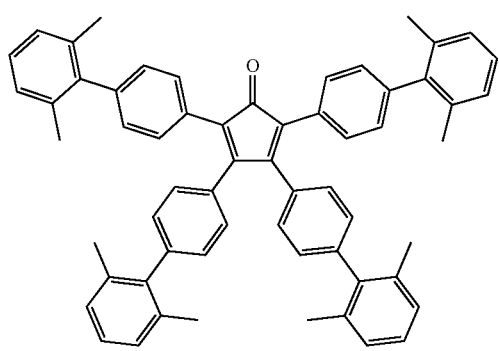
3-2(70%)
(v)
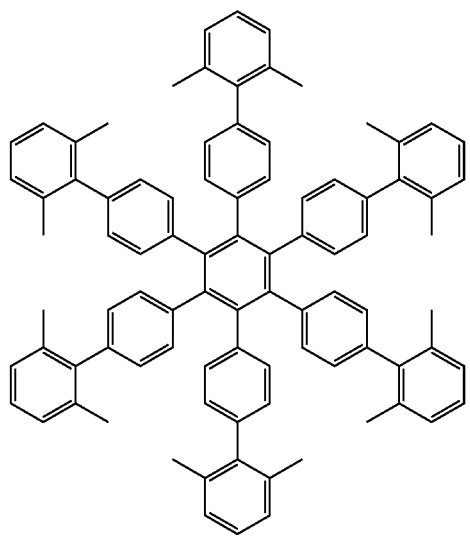
HPB-P2 (72%)
(vi)
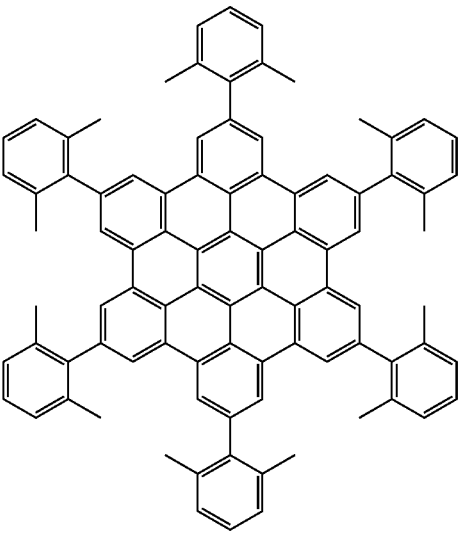
HBC-P2 (50%)

(iii) P2(2.5 equiv.), Pd(PPh$_3$)$_4$ (10 mol %), K$_2$CO$_3$ (5.0 equiv.), PhMe/EtOH/H$_2$O (v/v/v=15/2/5), 60° C., 12 h.
(iv)* P2(5.0 equiv.), Pd(PPh$_3$)$_4$ (20 mol %), K$_2$CO$_3$ (16 equiv.), PhMe/EtOH/H$_2$O (v/v/v=10/1/6), reflux, 12 h.
(v) Ph$_2$O, reflux, 2 d.
(vi) FeCl$_3$ (20 equiv.), Ch$_2$Cl$_2$/MeNo$_2$ (v/v=24/1), rt, 2 h.

Compound 3-1, Compound 3-2, and Ph$_2$O were put into a 500-mL round-bottom flask and heated in a nitrogen atmosphere under reflux for 48 hours. FeCl$_3$ (20 equiv.) and CH$_2$Cl$_2$/MeNO$_2$ (v/v=24/1) were added to the resulting intermediate HPB-P2(0.2 g, 72%) and then refluxed for 2 hours. After filtration of solids crystallized by addition of 1000 mL of methanol to the resulting mixture, the filtered product was dissolved in monochlorobenzene and filtered using a silica gel/Celite. After removal of an appropriate amount of the organic solvent, the resulting product was recrystallized with methanol to yield Compound 3 (0.1 g, Yield: 50%).

Synthesis Example 4: Synthesis of Compound 4 (GNR-P2

Compound 4 (GNR-P2) was synthesized according to the following reaction scheme.

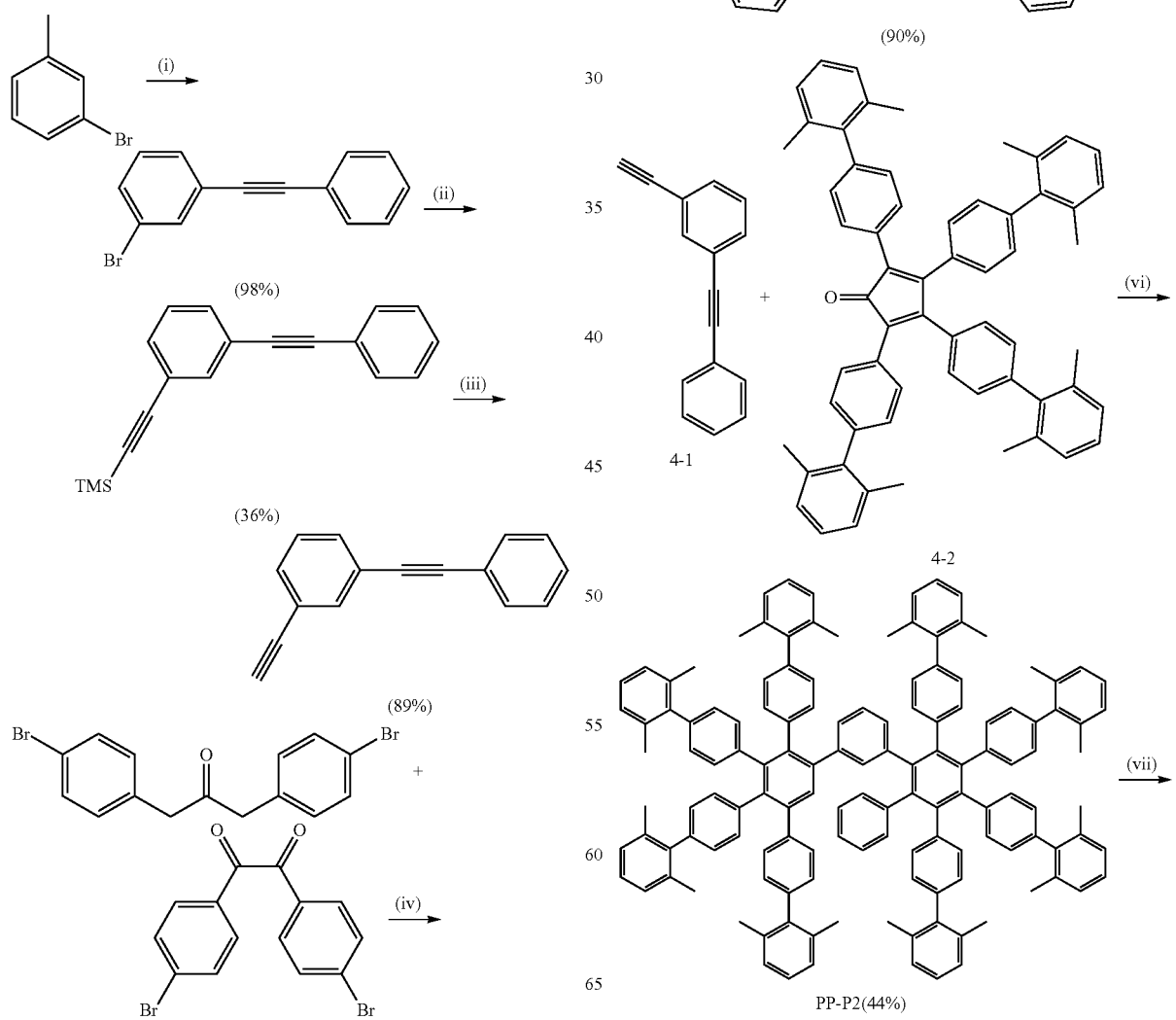

-continued

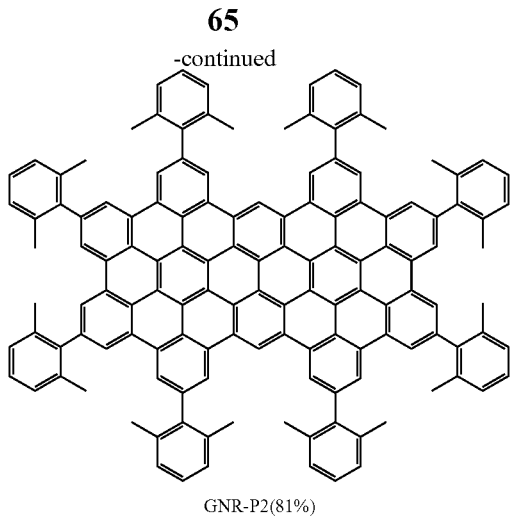

GNR-P2(81%)

(i) Pd(PPh$_3$)$_4$ CuI, Phenylacetylene, Piperidine, rt, 4 h
(ii) PdCl$_2$(PPh$_3$)$_2$, CuI, Phenylacetylene, THF, TEA, 60° C., 38 h
(iii) KF, MeOH, THF, 50° C., 8 h
(iv) t-BuOH, NEt$_4$OH, 80° C., 50 min
(v) P2, Pd(dppf)Cl$_2$CH$_2$Cl$_2$, Cs$_2$CO$_3$, toluene, 80° C., 24 h
(vi) Ph$_2$O, reflux, 49 h Compound 4-1, Compound 4-2, and Ph$_2$O were put into a 500-mL round-bottom flask and heated in a nitrogen atmosphere under reflux for 49 hours. FeCl$_3$, CH$_3$NO$_2$, and MC were added to the resulting intermediate PP-P2(0.1 g, 44%) and then refluxed for 48 hours. After filtration of solids crystallized by addition of 1000 mL of methanol to the resulting mixture, the filtered product was dissolved in monochlorobenzene and filtered using a silica gel/Celite. After removal of an appropriate amount of the organic solvent, the resulting product was recrystallized with methanol to yield Compound 4 (0.08 g, Yield: 80%).

Evaluation Example 1: X-Ray Diffraction (XRD) Analysis

Figure 3:
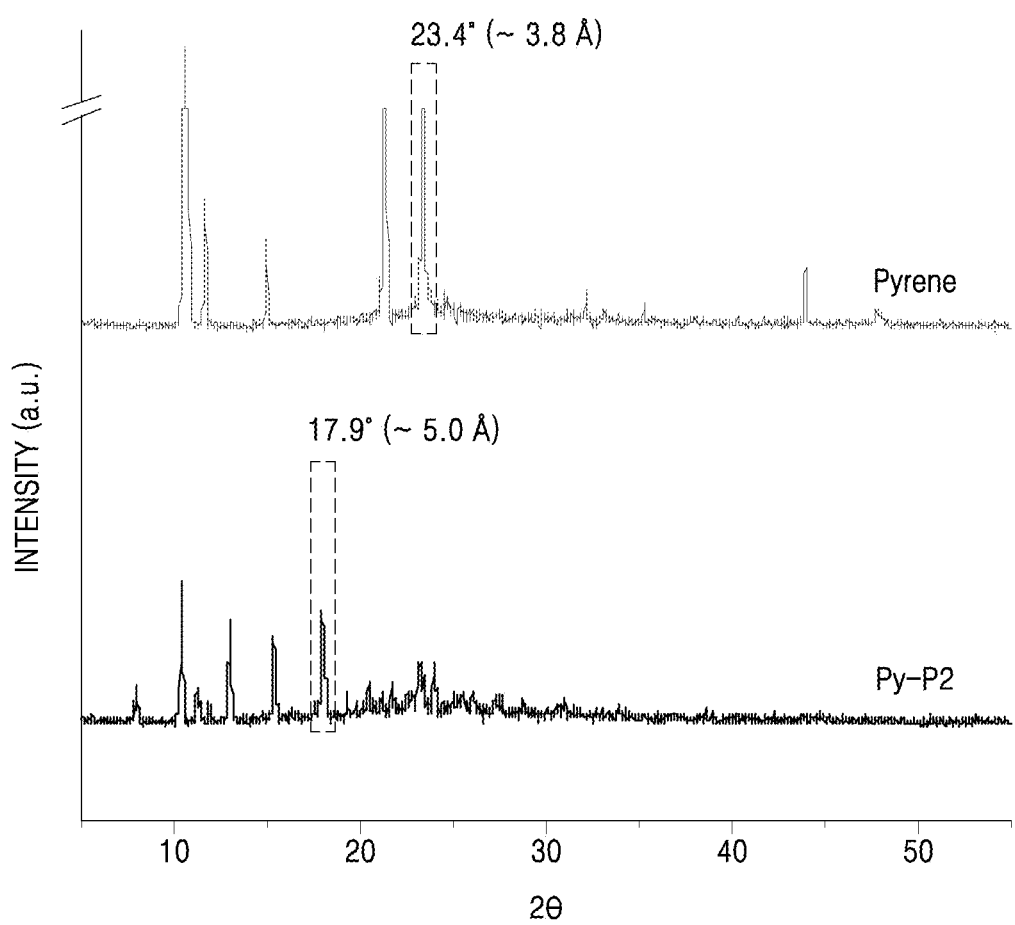
FIG. 3 is a comparative graph illustrating X-ray diffraction (XRD) analysis results of Compound 1 (Py-P2) of Synthesis Example 1 and pyrene.

To analyze the interplanar distance of Compound 1 obtained in Synthesis Example 1, X-ray diffraction (XRD) analysis was performed on Compound 1, and the results of comparison with pyrene (denoted as "Pyrene") are shown in FIG. 3.

As shown in FIG. 3, pyrene ("Pyrene") which was not functionalized exhibited a characteristic peak at 23.4° which corresponds to an interplanar distance of about 3.8 Å. Meanwhile, Compound 1 ("Py-P2") functionalized with dimethylphenyl exhibited a characteristic peak at 17.9°, which corresponds to an interplanar distance of about 5.0 Å. From these results, it was found that the functionalized polycyclic aromatic hydrocarbon compound had an increased interplanar distance due to the picket-fence effect resulting from the functional group, as compared with the non-functionalized case, and thus had a π-π stacking inhibitory effect.

(Preparation of Light-Emitting Solution and Light-Emitting Film)

Example 1

Preparation of light-emitting solution
Compound 1 (Py-P2) obtained in Synthesis Example 1 was dissolved in a THF solvent at a concentration of $10^{-5}$ M to prepare a light-emitting solution.
Preparation of light-emitting film
Compound 1 (Py-P2) obtained in Synthesis Example 1 was dissolved in THF at 1 wt %, and then spin-coated on a glass substrate to form a light-emitting film.

Example 2

A light-emitting solution and a light-emitting film were prepared through the same process as in Example 1, except that Compound 2 (Coro-P2) obtained in Synthesis Example 2 was used as a light-emitting material.

Example 3

A light-emitting solution and a light-emitting film were prepared through the same process as in Example 1, except that Compound 3 (HBC-P2) obtained in Synthesis Example 3 was used as a light-emitting material.

Example 4

A light-emitting solution and a light-emitting film were prepared through the same process as in Example 1, except that Compound 4 (GNR-P2) obtained in Synthesis Example 4 was used as a light-emitting material.

Comparative Example 1

A light-emitting solution and a light-emitting film were prepared through the same process as in Example 1, except that pyrene was used as a light-emitting material.

Comparative Example 2

A light-emitting solution and a light-emitting film were prepared through the same process as in Example 1, except that coronene was used as a light-emitting material.

Evaluation Example 2: Emission Characteristic Evaluation

Photoluminescence (PL) spectra of the light-emitting solutions and the light-emitting films of Examples 1 to 4 and Comparative Examples 1 and 2 were measured using a Hitachi F7000 spectrofluorometer equipped with a xenon lamp. For the light-emitting solution and the light-emitting films of Comparative Example 1 and Example 1, the measurement was performed using anthracene as a standard material at a $\lambda_{ex}$ of 330 nm. For the light-emitting solution and the light-emitting films of Comparative Example 2 and Examples 2 to 4, the measurement was performed using quinine sulfate as a standard material at a $\lambda_{ex}$ of 360 nm.

Figure 4A:
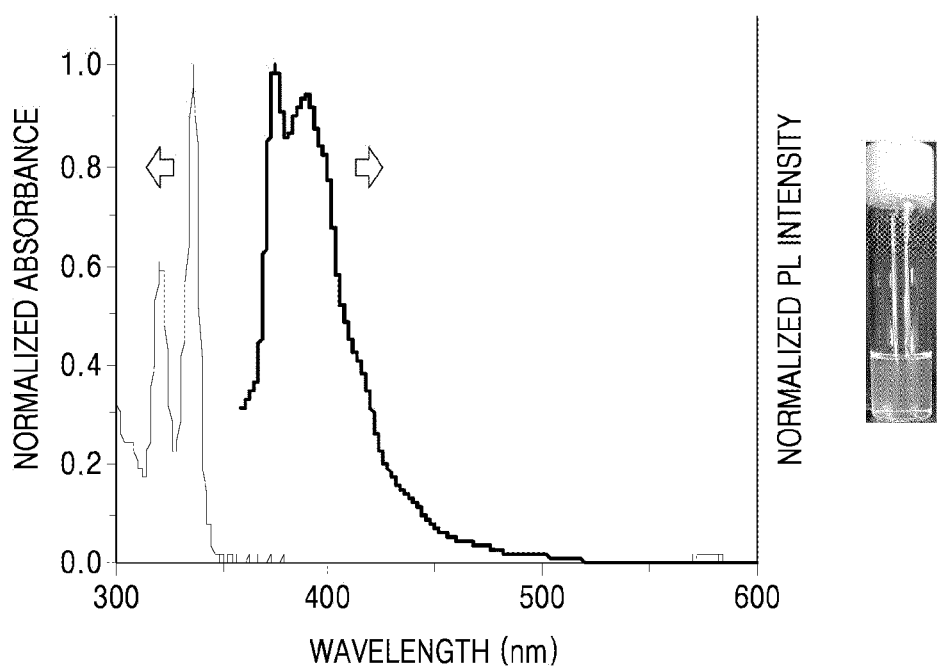
FIGS. 4A and 4B illustrate graphs of absorbance and emission spectra with respect to wavelength of a light-emitting solution and a light-emitting film of Comparative Example 1, respectively, and images of a light emission state.
Figure 4B:
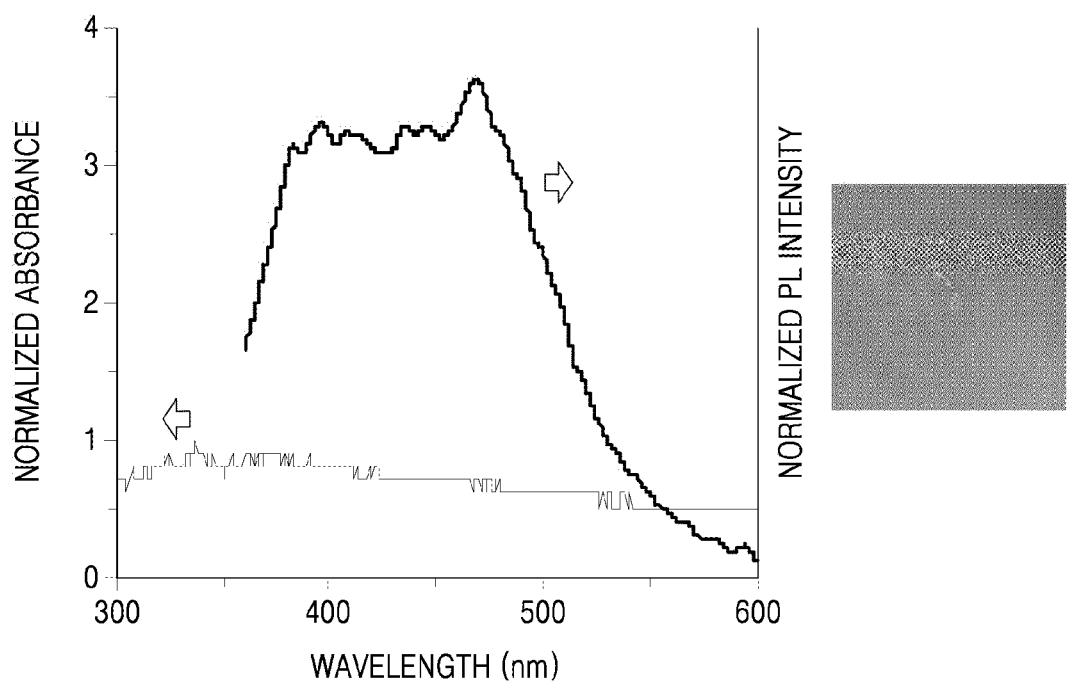

FIGS. 4A and 4B illustrate absorption and emission spectra with respect to wavelength of the light-emitting solution and the light-emitting film of Comparative Example 1, respectively, and images of a light emission state.

Figure 5A:
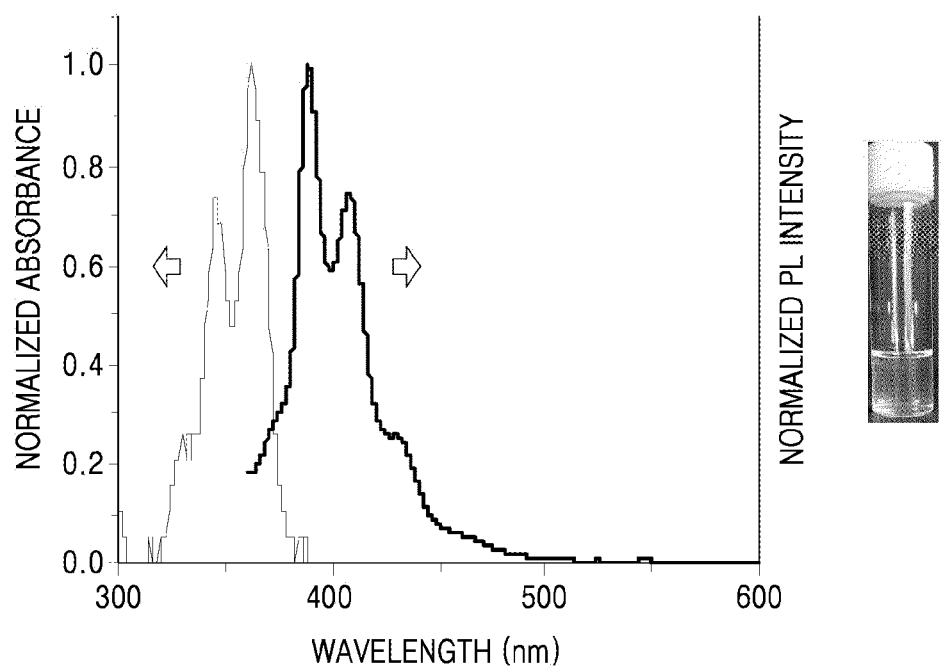
FIGS. 5A and 5B illustrate graphs of absorbance and emission spectra with respect to wavelength of a light-emitting solution and a light-emitting film of Example 1, respectively, and images of a light emission state.
Figure 5B:
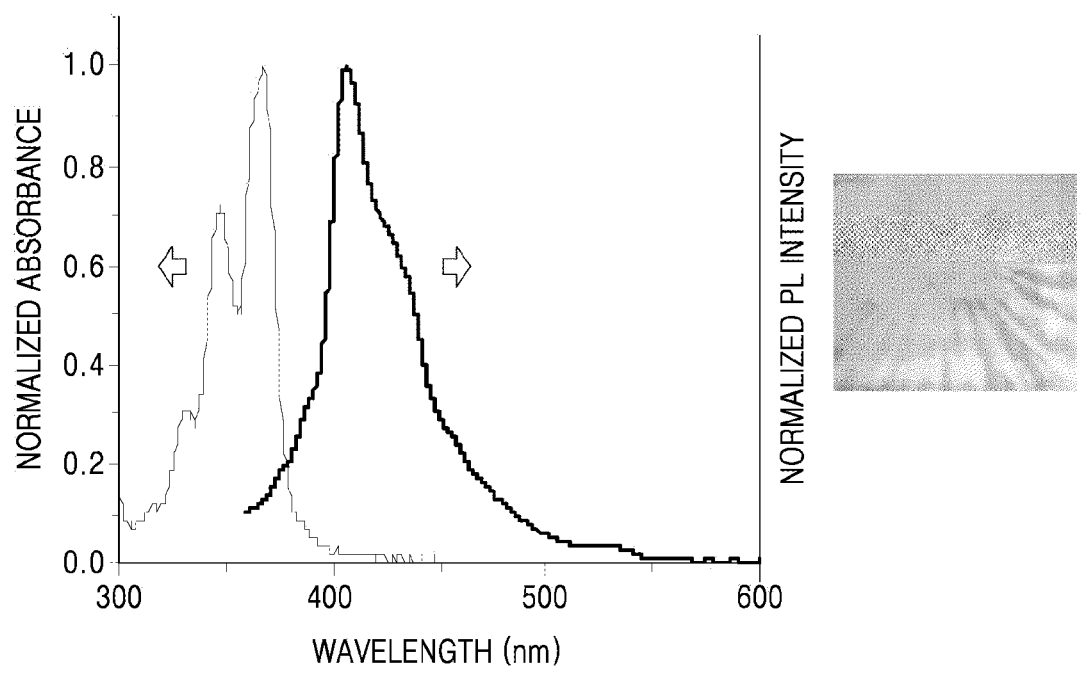

FIGS. 5A and 5B illustrate absorption and emission spectra with respect to wavelength of the light-emitting solution and the light-emitting film of Example 1, respectively, and images of a light emission state.

Figure 6A:
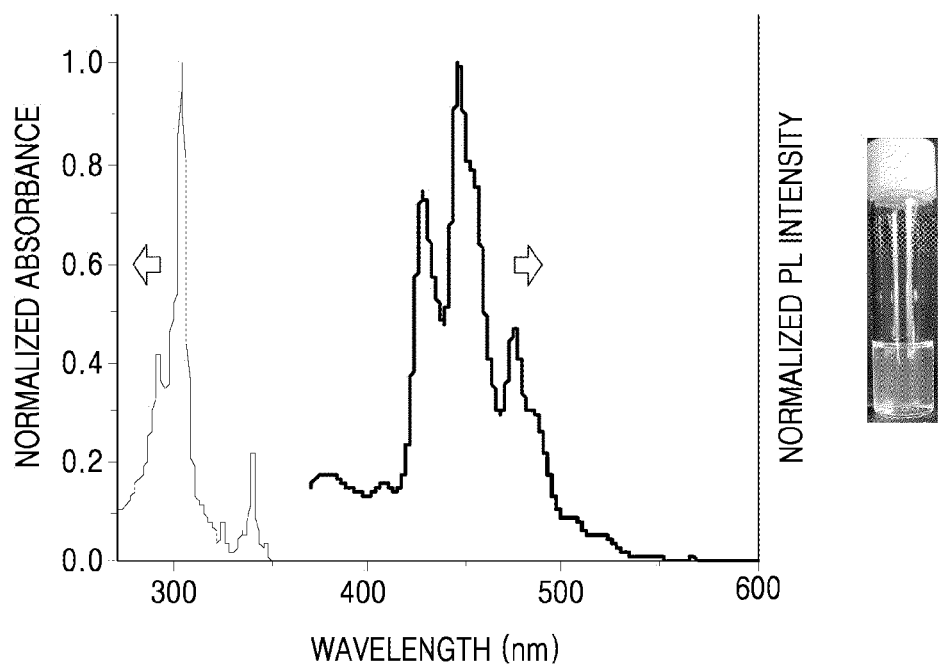
FIGS. 6A and 6B illustrate graphs of absorbance and emission spectra with respect to wavelength of a light-emitting solution and a light-emitting film of Comparative Example 2, respectively, and images of a light emission state.
Figure 6B:
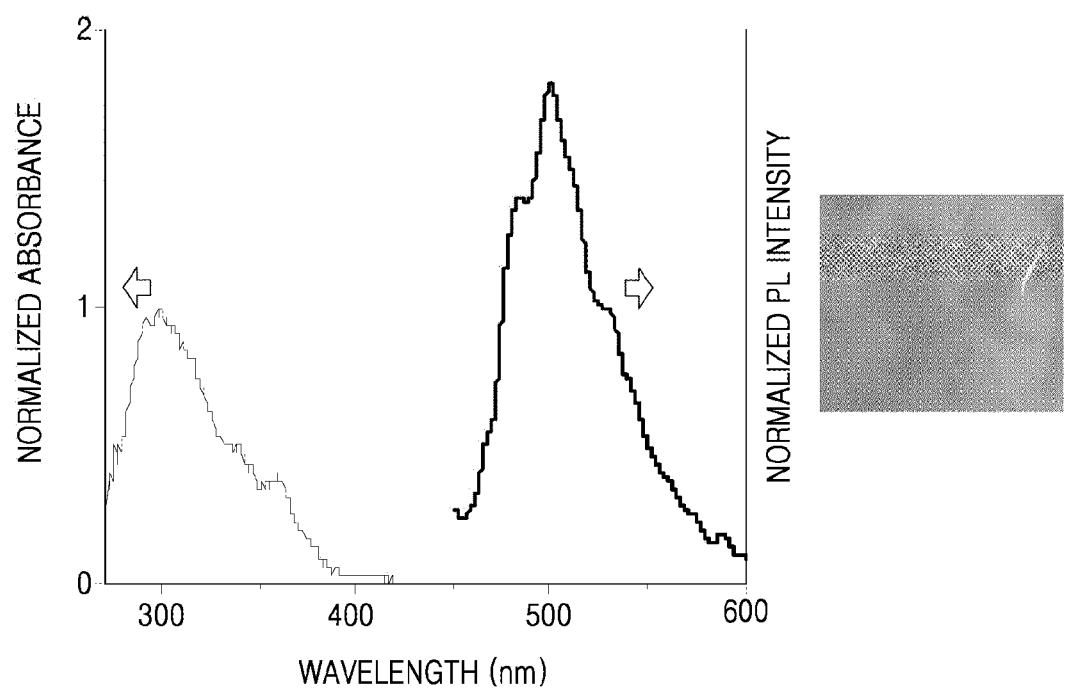

FIGS. 6A and 6B illustrate absorption and emission spectra with respect to wavelength of the light-emitting solution and the light-emitting film of Comparative Example 2, respectively, and images of a light emission state.

Figure 7A:
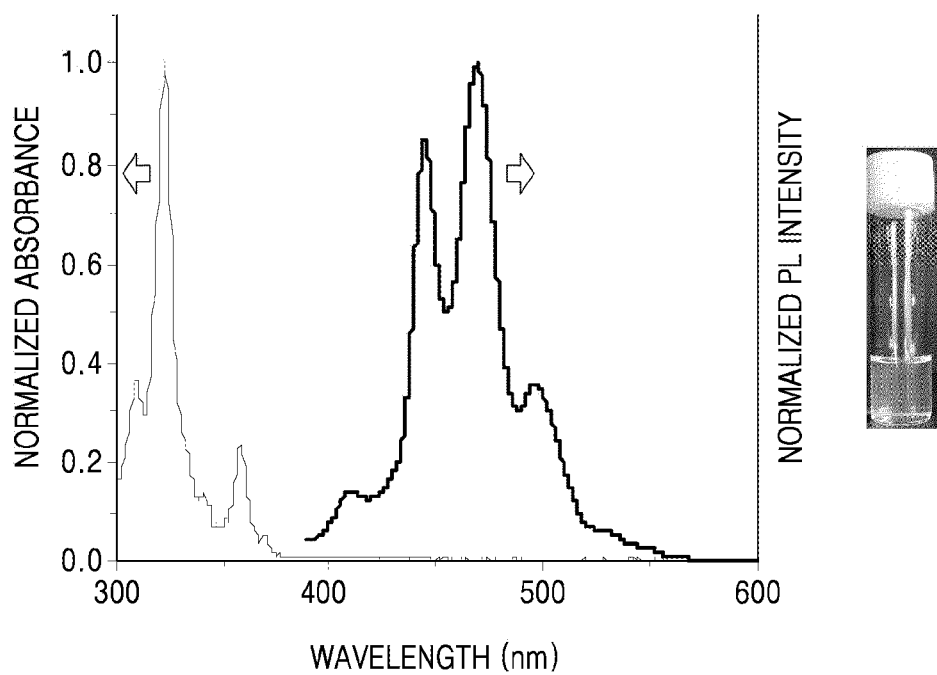
FIGS. 7A and 7B illustrate graphs of absorbance and emission spectra with respect to wavelength of a light-emitting solution and a light-emitting film of Example 2, respectively, and images of a light emission state.
Figure 7B:
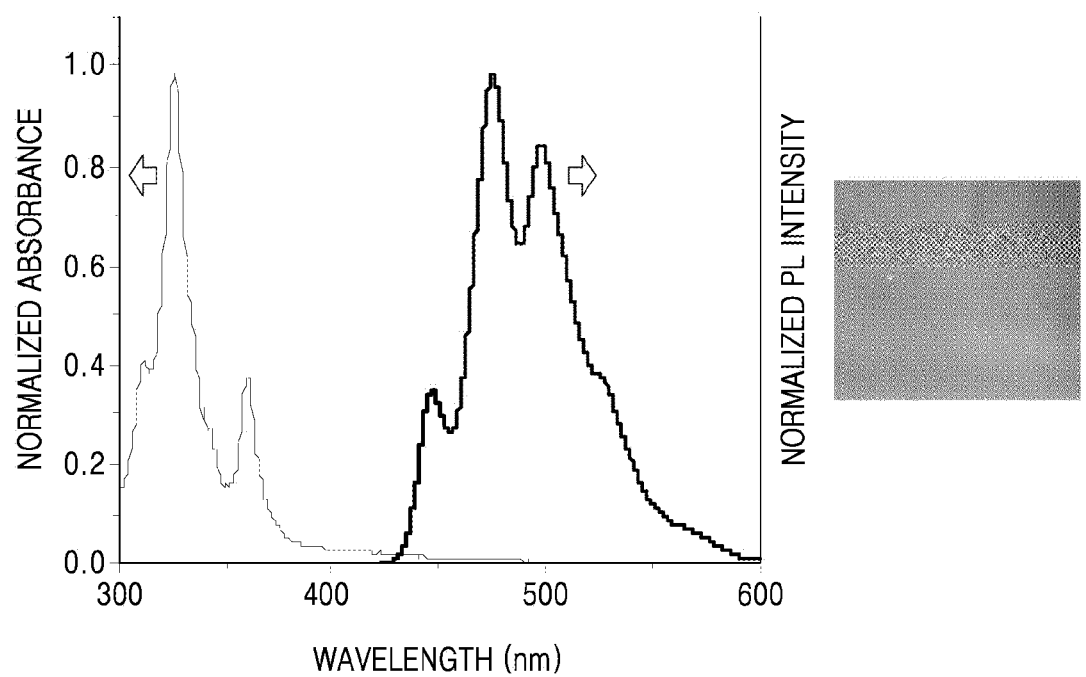

FIGS. 7A and 7B illustrate absorption and emission spectra with respect to wavelength of the light-emitting solution and the light-emitting film of Example 2, respectively, and images of a light emission state.

Figure 8A:
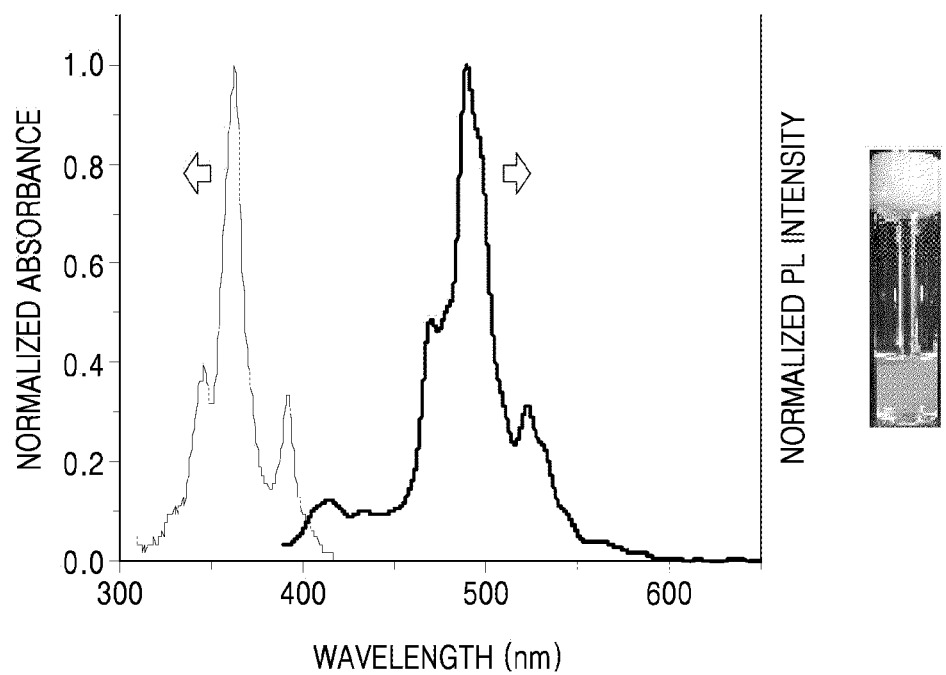
FIGS. 8A and 8B illustrate graphs of absorbance and emission spectra with respect to wavelength of a light-emitting solution and a light-emitting film of Example 3, respectively, and images of a light emission state.
Figure 8B:
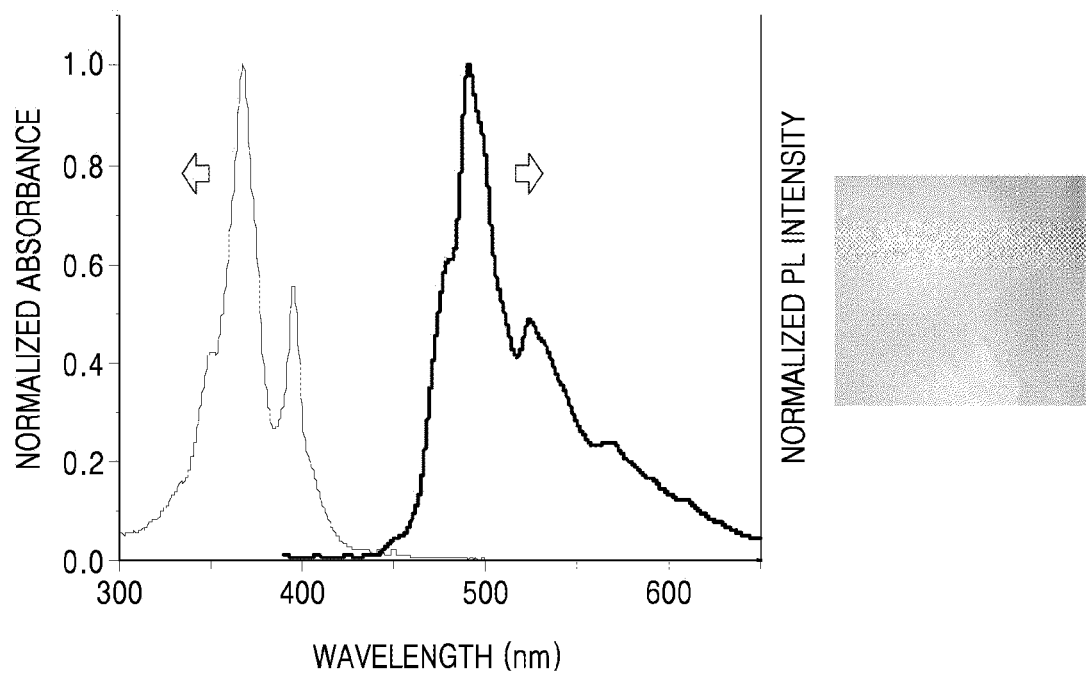

FIGS. 8A and 8B illustrate absorption and emission spectra with respect to wavelength of the light-emitting solution and the light-emitting film of Example 3, respectively, and images of a light emission state.

Figure 9A:
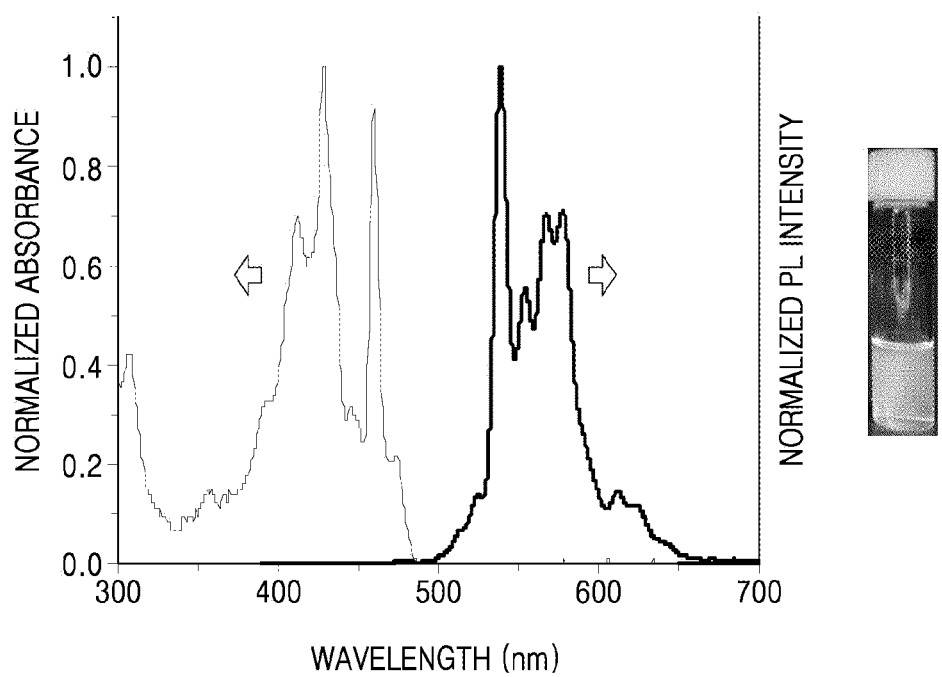
FIGS. 9A and 9B illustrate graphs of absorbance and emission spectra with respect to wavelength of a light-emitting solution and a light-emitting film of Example 4, respectively, and images of a light emission state.
Figure 9B:
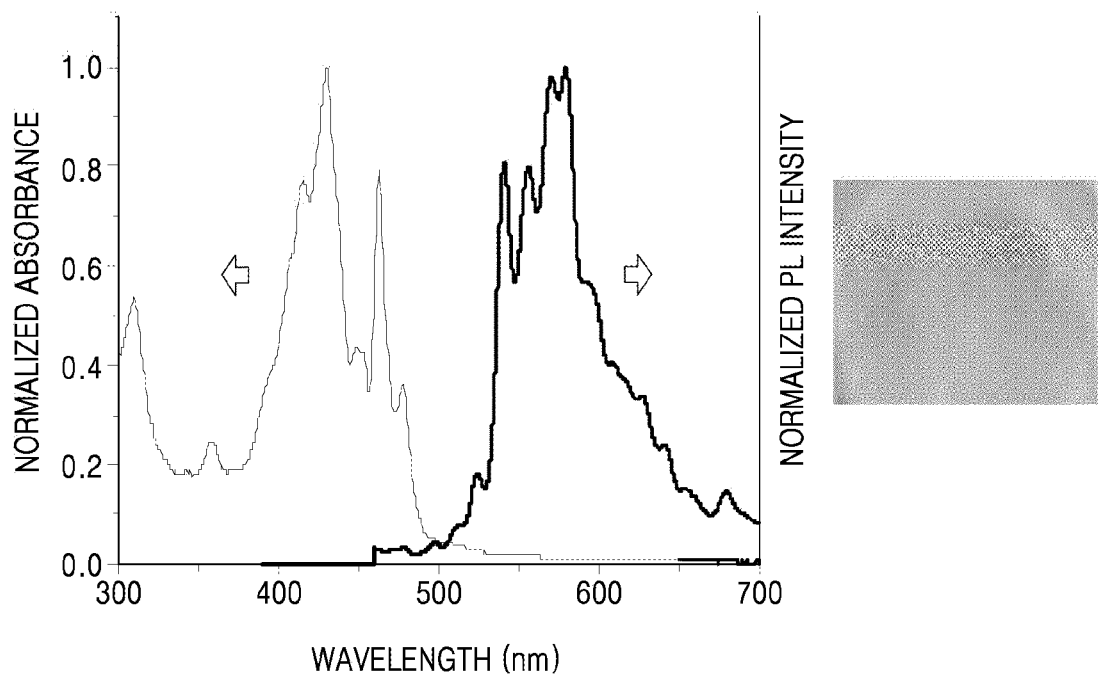

FIGS. 9A and 9B illustrate absorption and emission spectra with respect to wavelength of the light-emitting solution and the light-emitting film of Example 4, respectively, and images of a light emission state.

As shown in FIGS. 4A to 9B, it was found that the functionalized polycyclic aromatic hydrocarbon compounds effectively inhibited π-π stacking, as compared with a non-functionalized case, to exhibit improved emission efficiencies in solution and in a solid state. The functionalized polycyclic aromatic hydrocarbon compound exhibited excellent emission characteristics even in solution due to improved solubility, and a small red-shift in a solid state as a light-emitting film.

Light emission of the functionalized polycyclic aromatic hydrocarbon compounds in various wavelength bands may be obtained by controlling the core size.

Figure 10:
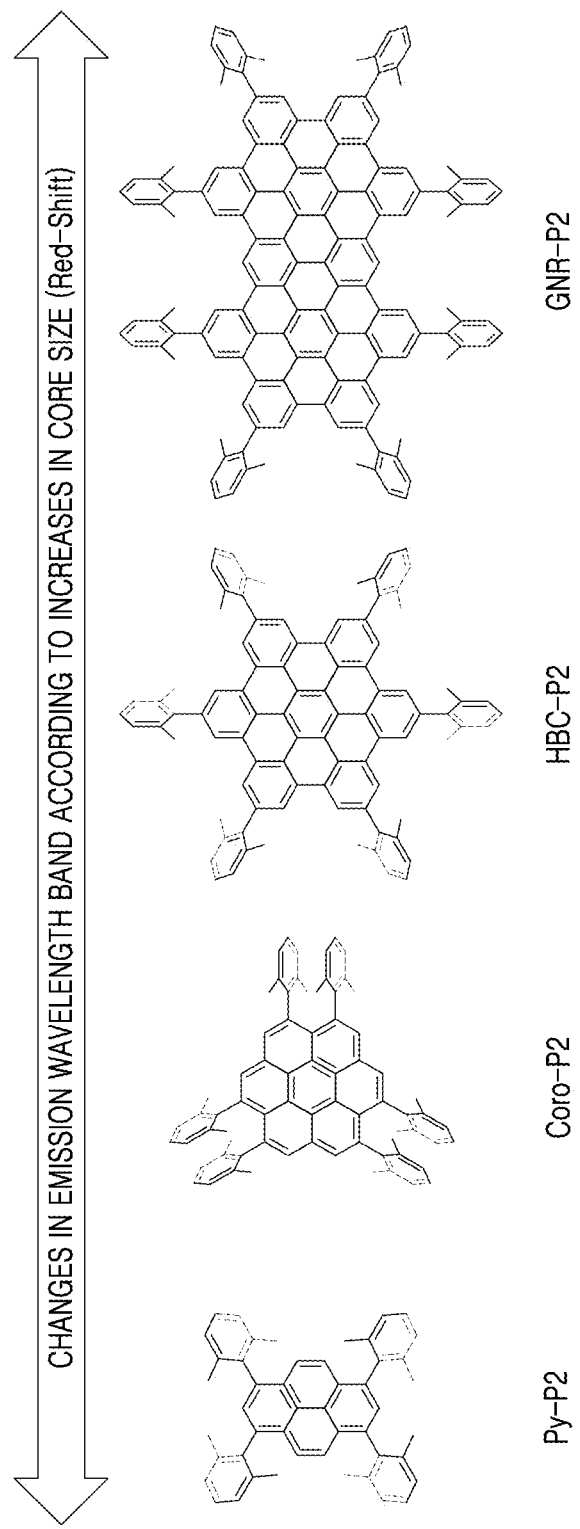
FIG. 10 is a schematic view showing changes in an emission wavelength band according to increases in core size of the compounds used in Examples 1 to 4.
Figure 11:
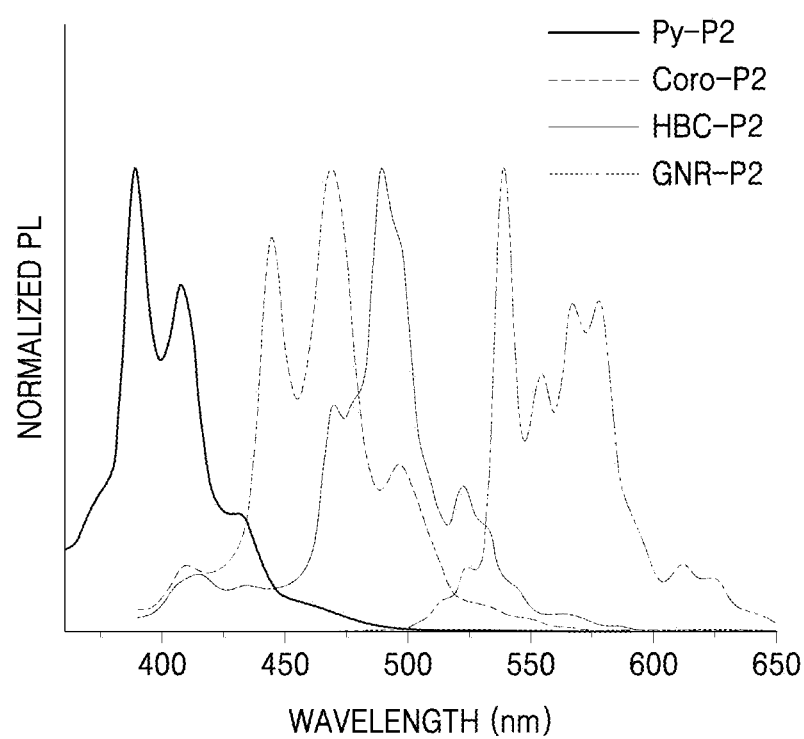
FIG. 11 is a comparative graph illustrating the emission spectra of the light-emitting solutions of Examples 1 to 4.

FIG. 10 is a schematic view showing changes in an emission wavelength band according to increases in core size of the compounds used in Examples 1 to 4. FIG. 11 is a comparative graph illustrating graph of the emission spectra of the light-emitting solutions of Examples 1 to 4. As shown in FIGS. 10 and 11, the functionalized polycyclic aromatic hydrocarbon compounds were found to exhibit a red-shift in the emission wavelength as the core size became larger.

Figure 12:
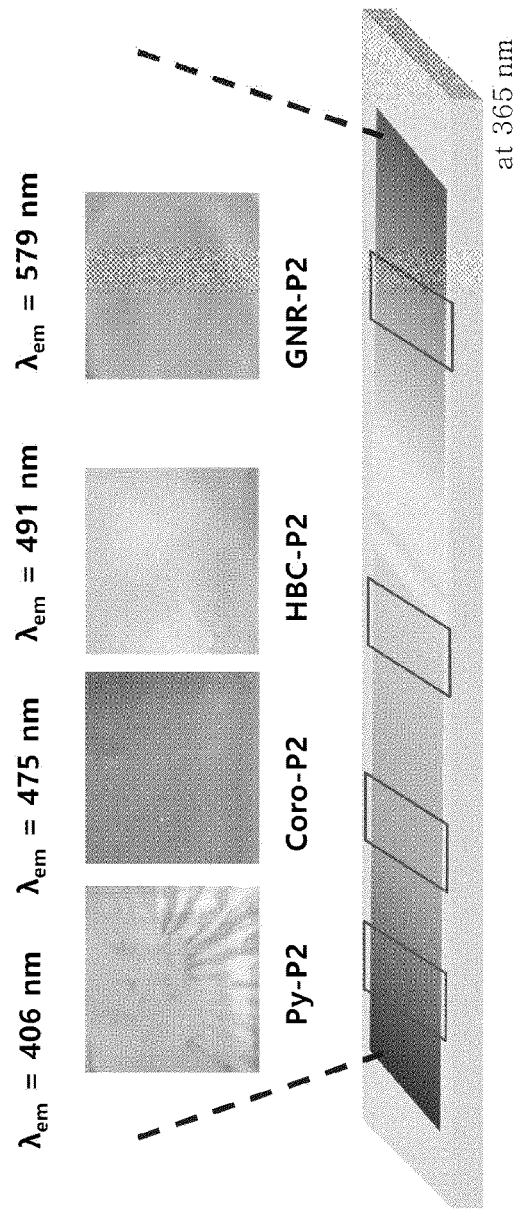
FIG. 12 is an image illustrating the emission characteristics of the light-emitting films of Examples 1 to 4.
Figure 13:
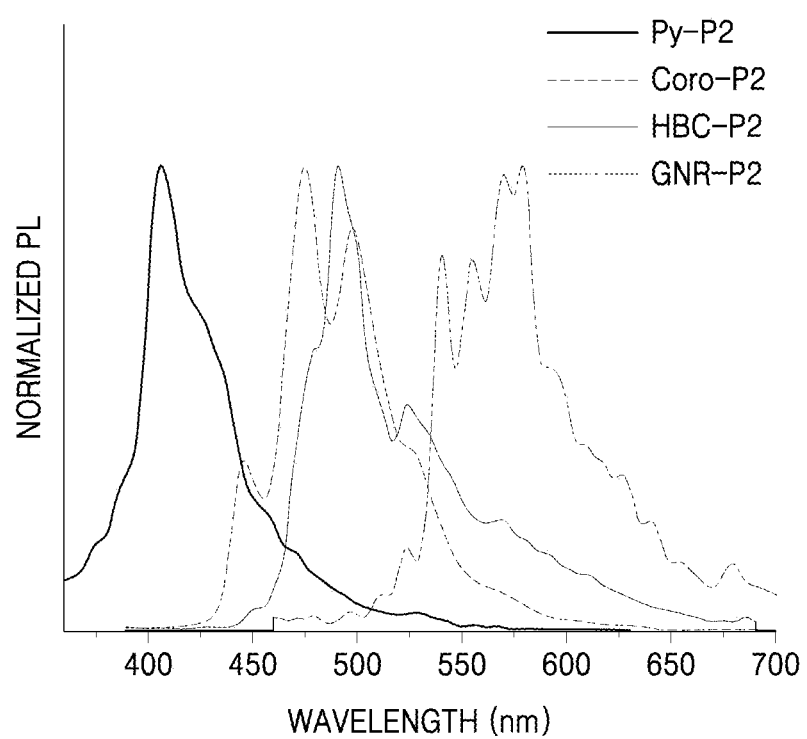
FIG. 13 is a comparative graph illustrating the emission spectra of the light-emitting films of Examples 1 to 4.

FIG. 12 is an image illustrating the light-emission characteristics of the light-emitting films of Examples 1 to 4. FIG. 13 is a comparative graph illustrating the emission spectra of the light-emitting films of Examples 1 to 4. As shown in FIGS. 12 and 13, the compounds used in Examples 1 to 4 were found to exhibit light-emission characteristics in the solid phase at similar wavelengths to those in the solution phase, due to the picket-fence effect.

Example 5

A glass substrate, on which a 1,500 Å ITO electrode (first electrode, anode) was formed, was cleaned in distilled water using ultrasonic waves. After the distilled water cleaning was completed, the glass substrate was cleaned with ultrasonic waves in a solvent such as isopropyl alcohol, acetone, and methanol, dried, provided to a plasma cleaner, cleaned for 5 minutes by oxygen plasma, and then provided to a vacuum deposition apparatus.

Compound HT3 and Compound HT-D2 were co-deposited on the ITO electrode of the glass substrate to form a hole injection layer having a thickness of 100 Å, Compound HT3 was deposited on the hole injection layer to form a hole transport layer having a thickness of 1,300 Å, and mCP was deposited on the hole transport layer to form an electron blocking layer having a thickness of 100 Å, thereby forming a hole transport region.

Compound 1 (host) and FIr6 (dopant, 10 wt %) were co-deposited on the hole transport region to form an emission layer having a thickness of 400 Å.

BCP was vacuum-deposited on the emission layer to form a hole blocking layer having a thickness of 100 Å, Compound ET3 and LiQ were vacuum-deposited on the hole blocking layer to form an electron transport layer having a thickness of 300 Å, LiQ was deposited on the electron transport layer to form an electron injection layer having a thickness of 10 Å, and Al was deposited on the electron injection layer to form a second electrode (cathode) having a thickness of 1,200 Å, thereby completing the manufacture of an organic light-emitting device.

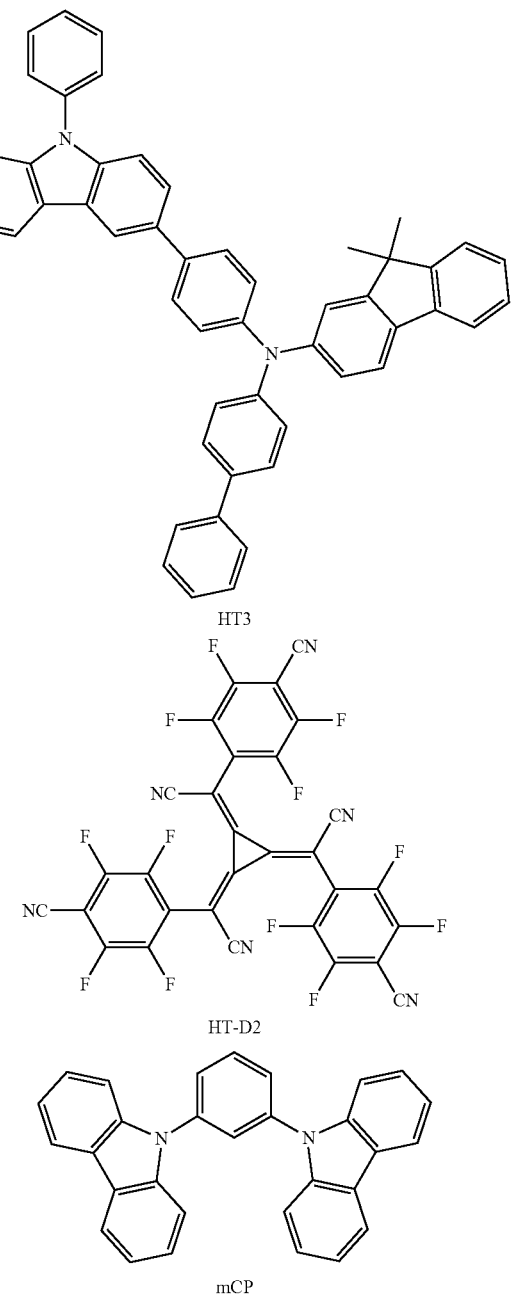

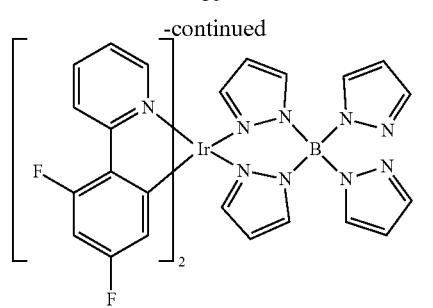

FIr6

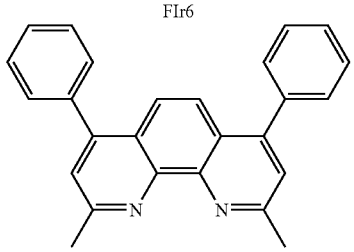

BCP

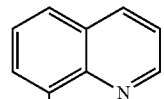

ET3

Example 6

An organic light-emitting device was manufactured in the same manner as in Example 5, except that Compound 2 was used instead of Compound 1 as a host to form an emission layer.

Example 7

An organic light-emitting device was manufactured in the same manner as in Example 5, except that Compound 3 was used instead of Compound 1 as a host to form an emission layer.

Example 8

An organic light-emitting device was manufactured in the same manner as in Example 5, except that Compound 4 was used instead of Compound 1 as a host to form an emission layer.

Comparative Example 3

An organic light-emitting device was manufactured in the same manner as in Example 5, except that pyrene was used instead of Compound 1 as a host to form an emission layer.

Comparative Example 4

An organic light-emitting device was manufactured in the same manner as in Example 5, except that coronene was used instead of Compound 1 as a host to form an emission layer.

As described above, according to the one or more embodiments, by inclusion of a functionalized polycyclic aromatic hydrocarbon compound which is structurally stable and exhibits high light-emission characteristics due to inhibition of the aggregation resulting from π-π stacking, a light-emitting material may have high efficiency and long lifespan characteristics.

It should be understood that embodiments described herein should be considered in a descriptive sense only and not for purposes of limitation.

Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of inventive concepts as defined by the following claims.

What is claimed is:

1. A functionalized polycyclic aromatic hydrocarbon compound represented by any one of Formulae 2 to 7:

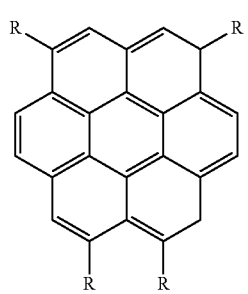

<Formula 2>

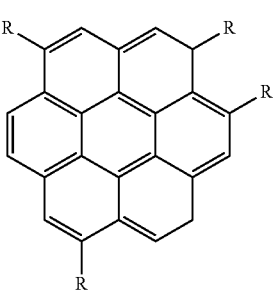

<Formula 3>

-continued

<Formula 4>

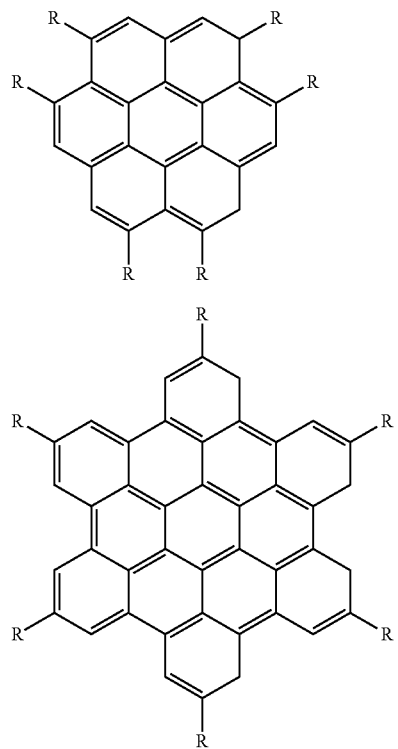

<Formula 5>

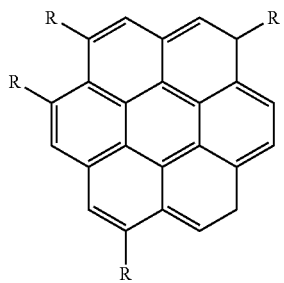

<Formula 6>

<Formula 7>

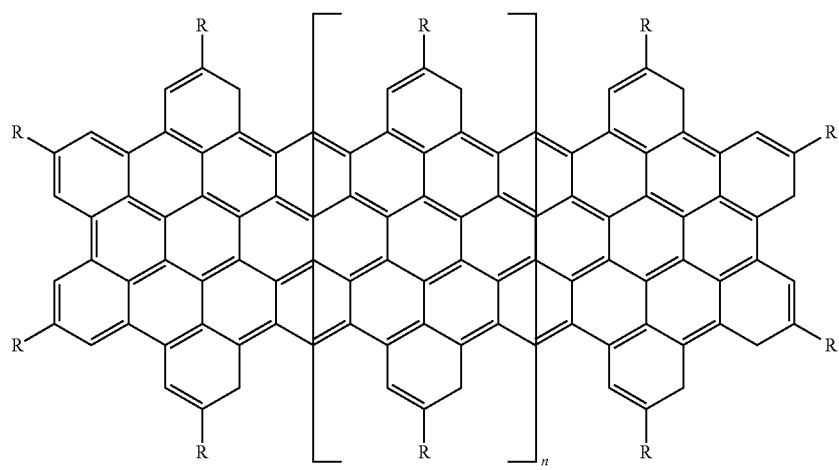

wherein, in Formulae 2 to 7,
R is

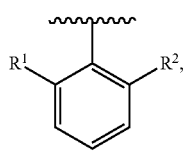

R¹ and R² are each independently selected from a fluoro group (—F), a chloro group (—Cl), a bromo group (—Br), an iodo group (—I), a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —N(Q₁)(Q₂), —Si(Q₃)(Q₄)(Q₅), and —B(Q₆)(Q₇), Q₁ to Q₇ are each independently selected from hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, and n in Formula 7 is an integer of 0 to 10.

2. The functionalized polycyclic aromatic hydrocarbon compound of claim 1, wherein $R^1$ and $R^2$ in R are each independently a fluoro group (—F), an unsubstituted $C_1$-$C_{10}$ alkyl group, an unsubstituted $C_6$-$C_{10}$ aryl group, a $C_1$-$C_{10}$ alkyl group substituted with a fluoro group, or a $C_6$-$C_{10}$ aryl group substituted with a fluoro group.

3. The functionalized polycyclic aromatic hydrocarbon compound of claim 1, wherein $R^1$ and $R^2$ in R are each independently an unsubstituted $C_1$-$C_5$ alkyl group.

4. The functionalized polycyclic aromatic hydrocarbon compound of claim 1, wherein $R^1$ and $R^2$ in R are each independently a methyl group or an ethyl group.

5. The functionalized polycyclic aromatic hydrocarbon compound of claim 1, wherein in one to six of the R groups in Formulae 2 to 6, $R^1$ and $R^2$ are each an unsubstituted $C_1$-$C_5$ alkyl group.

6. The functionalized polycyclic aromatic hydrocarbon compound of claim 1, wherein in six or more of the R groups in Formula 7, $R^1$ and $R^2$ are each an unsubstituted $C_1$-$C_5$ alkyl group.

7. The functionalized polycyclic aromatic hydrocarbon compound of claim 1, wherein the functionalized polycyclic aromatic hydrocarbon compound comprises one compound from among compounds represented by Formula 2a to Formula 7c:

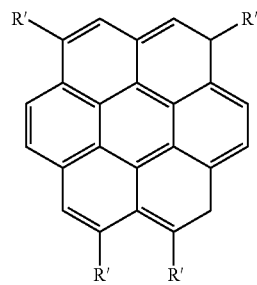

<Formula 2a>

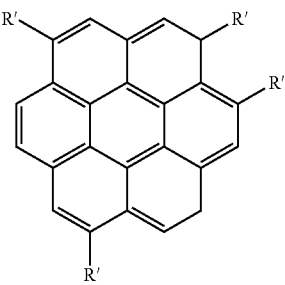

<Formula 3a>

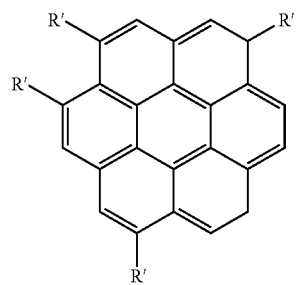

<Formula 4a>

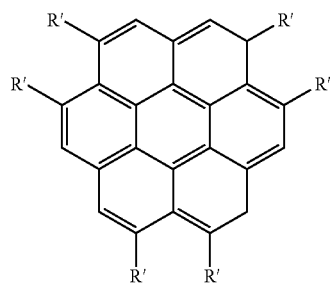

<Formula 5a>

<Formula 6a>
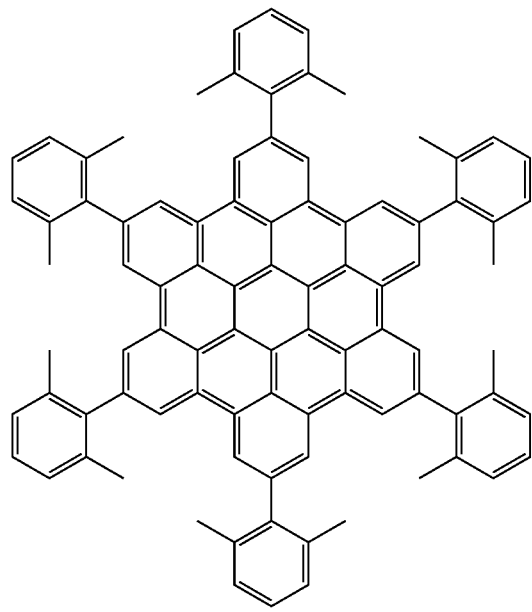
<Formula 7a>
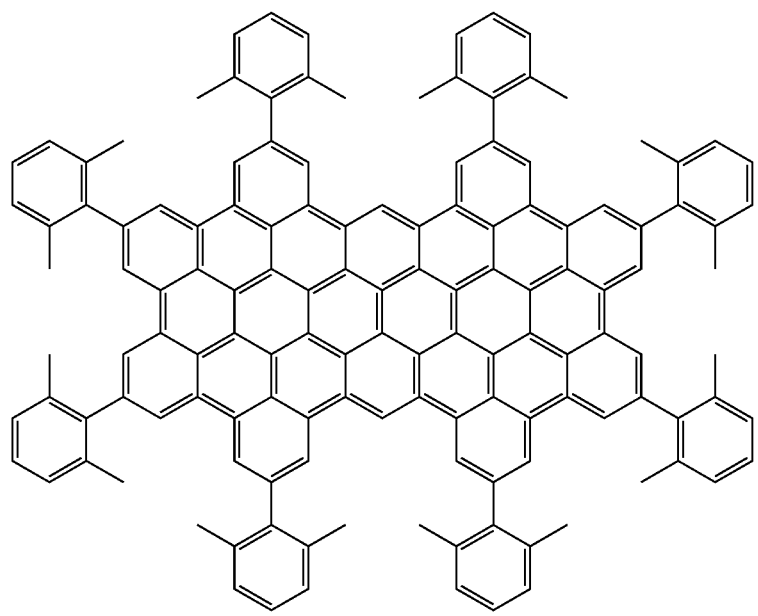

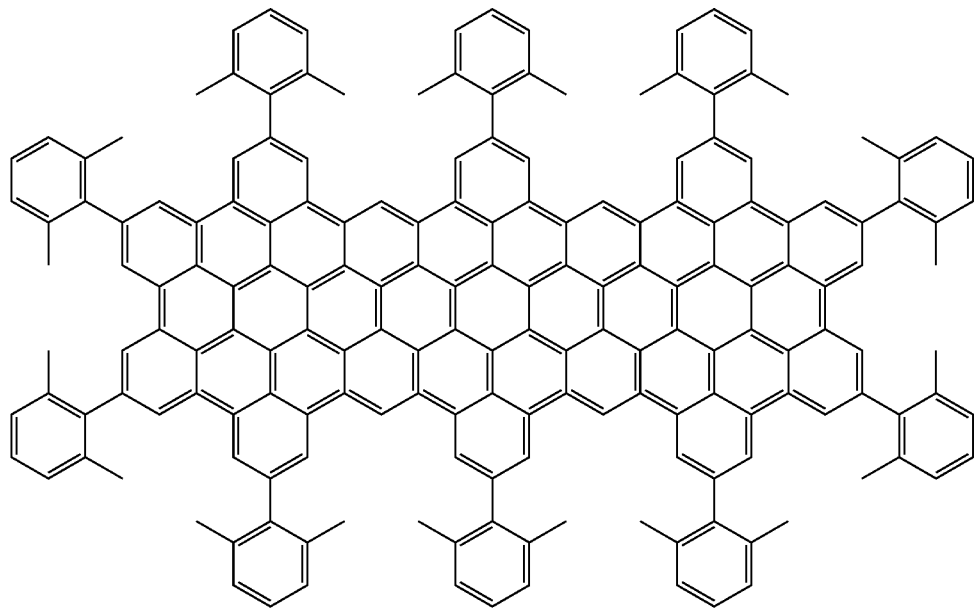

<Formula 7b>

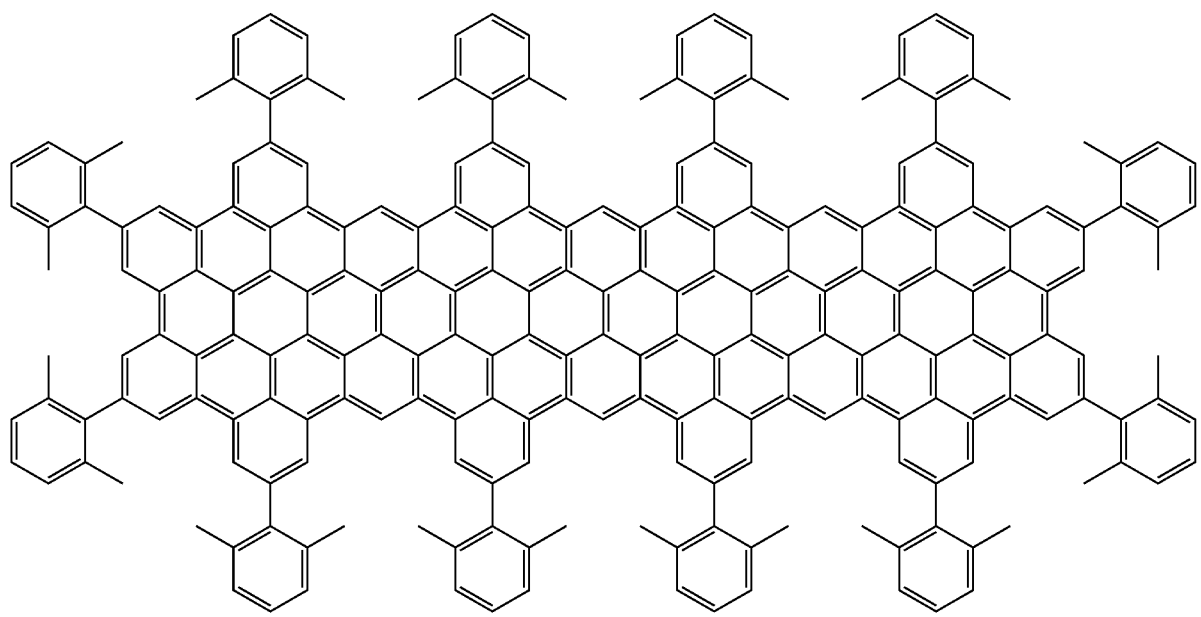

<Formula 7c> wherein, in Formulae 2a to 5a R' is

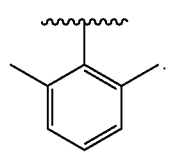

8. A light-emitting material comprising:
the functionalized polycyclic aromatic hydrocarbon compound according to claim 1.

9. The light-emitting material of claim 8, wherein the light-emitting material is in a solid state or in solution.

10. The light-emitting material of claim 8, wherein the light-emitting material has properties of light emission in a wavelength range of about 350 nm to about 650 nm.

11. A light-emitting device comprising:
the functionalized polycyclic aromatic hydrocarbon compound according to claim 1.

12. An organic light-emitting device comprising:
a first electrode;
a second electrode; and
an organic layer including an emission layer disposed between the first electrode and the second electrode,
wherein the organic layer includes the functionalized polycyclic aromatic hydrocarbon compound according to claim 1.

13. The organic light-emitting device of claim 12, wherein
the first electrode is an anode,
the second electrode is a cathode, and
the organic layer includes a hole transport region and an electron transport region,
the hole transport region is between the first electrode and the emission layer the hole transport region includes at least one of a hole injection layer, a hole transport layer,
the electron transport region is between the emission layer and the second electrode and the electron transport region includes at least one of a hole blocking layer, an electron transport layer, and an electron injection layer.

14. The organic light-emitting device of claim 12, wherein the emission layer includes the polycyclic aromatic hydrocarbon compound.

15. The organic light-emitting device of claim 14, wherein the emission layer exhibits properties of light emission in a wavelength range of about 350 nm to about 650 nm.

* * * * *